US007700575B2

(12) United States Patent  
Andrew et al.

(10) Patent No.: US 7,700,575 B2  
(45) Date of Patent: Apr. 20, 2010

(54) METHODS OF TREATING OCULAR CONDITIONS

(76) Inventors: Huang Andrew, 906 Dartmouth Pl. SE., Minneapolis, MN (US) 55414; Ching Yuan, 10005 Greenbrier Rd., Minnetonka, MN (US) 55305; Emily Zins, 2165 Zealand Ave. North, Golden Valley, MN (US) 55427

( * ) Notice: Subject to any disclaimer, the term of this patent is extended or adjusted under 35 U.S.C. 154(b) by 249 days.

(21) Appl. No.: 11/546,940

(22) Filed: Oct. 12, 2006

(65) Prior Publication Data

US 2007/0087989 A1  Apr. 19, 2007

Related U.S. Application Data

(63) Continuation of application No. PCT/US2005/012607, filed on Apr. 13, 2005.

(60) Provisional application No. 60/561,779, filed on Apr. 13, 2004.

(51) Int. Cl.  
*A01N 43/04* (2006.01)  
*A61K 31/70* (2006.01)

(52) U.S. Cl. .......................................................... 514/44

(58) Field of Classification Search .................... 514/44  
See application file for complete search history.

(56) References Cited

U.S. PATENT DOCUMENTS

| 6,403,307 | B1 * | 6/2002 | Stone et al. ................. 435/6 |
| 6,475,724 | B1 * | 11/2002 | Nguyen et al. .............. 435/6 |
| 6,506,559 | B1 * | 1/2003 | Fire et al. ................... 435/6 |
| 2007/0031844 | A1 * | 2/2007 | Khvorova et al. ............. 435/6 |

OTHER PUBLICATIONS

Tuschl et al. (The siRNA user guide, 2001).*  
Hammond et al. (Nature, 2001, vol. 2, pp. 110-119).*  
Fauss D.J. et al., Lutjen-Drecoll, E. (Ed.), "Glucocorticoid (GC) Effects on HTM cells: Biochemical approaches and growth factor reponses", *Basic Aspects of Glaucoma Research III*,. Schattauer Verlag, New York, NY, pp. 319-330 (1993).  
Polansky et al., "Trabecular Meshwork Cell Culture in Glaucoma Research: Evaluation of Biological Activity and Structural Properties of Human Trabecular Cells in Vitro", *The Journal of the American Academy of Ophthalmology*, vol. 91, No. 6, pp. 580-595, (1984).  
Pang et al., "Preliminary characterization of a transformed cell strain derived from human trabecular meshwork", *Current Eye Research*, vol. 13, No. 1, 1994, pp. 51-63.  
Kahn and Milton, "Revised Framingham Eye Study Prevalence of Glaucoma and Diabetic Retinopathy", *American Journal of Epidemiology*, vol. 111, No. 6, © 1980, pp. 769-776.  
Bally et al., "Biological barriers to cellular delivery of lipid-based DNA carriers", *Advanced Drug Delivery Reviews*, vol. 38, Elsevier Science B.V. © 1999, pp. 291-315.

Tamm, E.R., "Myocilin and glaucoma: facts and ideas", *Progress in Retinal and Eye Research*, vol. 21, Elsevier Science © 2002, pp. 395-428.  
Fingert et al., "Myocilin Glaucoma", *Survey of Ophthamology*, vol. 47, No. 6, Elsevier Science, Inc. © 2002, pp. 547-561.  
Wei et al., "A Role for Caveolin and the Urokinase Receptor in Integrin-mediated Adhesion and Signaling", © The Rockefeller University Press, *The Journal of Cell Biology*, vol. 144, No. 6, Mar. 22, 1999, pp. 1285-1294.  
Derwent, D., "Recent patents in drug delivery", *Nature Biotech.*, Jan. 2002, vol. 20, p. 93.  
Zimmer et al., "Pharmacokinetic and Pharmacodynamic Aspects of an Ophthalmic Pilocarpine Nanoparticle-Delivery System", *Pharmaceutical Research*, vol. 11, No. 10, © 1994 Plenum Publishing Corporation, pp. 1435-1442.  
Yu et al., "RNA interference by expression of short-interfering RNAs and hairpin RNAs in mammalian cells", *PNAS*, Apr. 30, 2002, vol. 99, No. 9, pp. 6047-6052.  
Yoon, "Mutations of the TIGR/MYOC Gene in primary Open-Angle Glaucoma in Korea", Am. J. Hum. Gen., vol. 64, © 1999 by The American Society of Human Genetics, pp. 1775-1778.  
Wordinger et al., "Human Trabecular Meshwork Cells Secrete Neurotrophins and Express Neurotrophin Receptors (Trk)", *Investigative Ophthalmology & Visual Science*, Nov. 2000, vol. 41, No. 12, Copyright © Association for Research in Vision and Ophthalmology, pp. 3833-3841.  
Wiggs and Vollrath, "Molecular and Clinical Evaluation of a Patient Hemizygous for TIGR/MYOC", *Arch Ophthalmology*, vol. 119, Nov. 2001, © 2001 American Medical Association, pp. 1674-1678.  
Volonte et al., "Flotillins/Cavatellins Are Differentially Expressed in Cells and Tissues and Form a Hetero-oligomeric Complex with Caveolins in Vivo", *The Journal of Biological Chemistry*, vol. 274, No. 18, Issue of Apr. 30, 1999, pp. 12702-12709, © 1999 by The American Society for Biochemistry and Molecular Biology, Inc.  
Ueda and Yue, "Distribution of Myocilin and Extracellular Matrix Components in the Corneoscleral Meshwork of Human Eyes", *Investigative Ophthalmology & Visual Science*, Nov. 2003, vol. 44, No. 11, Copyright © Association for Research in Vision and Ophthalmology, pp. 4772-4779.  
Szczesna-Skorupa et al., "Gene Expression Changes Associated with the Endoplasmic Reticulum Stress Response Induced by Microsomal Cytochrome P450 Overproduction", *The Journal of Biological Chemistry*, vol. 279, No. 14, Apr. 2, 2004, pp. 13953-13961, © 2004 by The American Society for Biochemistry and Molecular Biology, Inc.  
Sohn et al., "Expression of Wild-Type and Truncated Myocilins in Trabecular Meshwork Cells: Their Subcellular Localizations and Cytotoxicities", *Investigative Ophthalmology & Visual Science*, vol. 43, No. 12, Dec. 2002, pp. 3680-3685, Copyright © Association for Research in Vision and Ophthalmology.  
Russell et al., "The Presence and Properties of Myocilin in the Aqueous Humor", *Investigative Ophthalmology & Visual Science*, vol. 42, No. 5, Apr. 2001, pp. 983-986, Copyright © Association for Research in Vision and Ophthalmology.

(Continued)

*Primary Examiner*—Brian Whiteman  
(74) *Attorney, Agent, or Firm*—Colin L. Fairman; Fulbright & Jaworski LLP

(57) ABSTRACT

The present invention provides siRNA specific for myocilin and mutant myocilin, and methods of treating ocular conditions and/or diseases.

23 Claims, 7 Drawing Sheets

OTHER PUBLICATIONS

Qaddoumi et al., "The Characteristics and Mechanisms of Uptake of PLGA Nanoparticles in Rabbit Conjunctival Epithelial Cell Layers", *Pharmaceutical Research*, vol. 21, No. 4, Apr. 2004, pp. 641-648, © 2004 Plenum Publishing Corporation.

Polansky et al., "Human Trabecular Cells—I. Establishment in tissue culture and growth characteristics", *Assoc. For Res. in Vis. and Ophthal., Inc.*, © 1979, pp. 1043-1049.

Paddison et al., "Short hairpin RNAs (shRNAs) induce sequence-specific silencing in mammalian cells", *Genes and Development*, © 2002 Cold Spring Harbor Laboratory Press, pp. 16: 948-958.

Ortego, J. et al., "Cloning and Characterization of subtracted cDNAs from a human ciliary body library encoding TIGR, a protein involved in juvenile open angle glaucoma with homology to myosin and olfactomedin", *FEBS*, 413, © 1997 Federation of European Biochemical Societies, pp. 349-353.

Miller et al., "Allele-specific silencing of dominant disease genes", *PNAS*, Jun. 10, 2003, vol. 100, No. 12, pp. 7195-7200.

Martinez et al., "Synthetic small inhibiting RNAs: Efficient tools to inactivate oncogenic mutations and restore p53 pathways", *PNAS*, Nov. 12, 2002, vol. 99, No. 23, pp. 14849-14854.

Lam et al., "Truncations in the *TIGR* Gene in individuals with and without Primary Open-Angle Glaucoma", *Investigative Ophthalmology & Visual Science*, May 2000, vol. 41, No. 6, Copyright © Association for Research in Vision and Ophthalmology, pp. 1386-1391.

Lutjen-Drecoll et al., "Localization of the Stress Proteins αB-Crystallin and Trabecular Meshwork Inducible Glucocorticoid Response Protein in Normal and Glaucomatous Trabecular Meshwork", *Investigative Ophthalmology & Visual Science*, Mar. 1998, vol. 39, No. 3, Copyright © Association for Research in Vision and Ophthalmology, pp. 517-525.

Koltover et al., "DNA Condensation in two dimensions", *PNAS*, Dec. 19, 2000, vol. 97, No. 26, pp. 14046-14051.

Kim, et al., "Targeted Disruption of the Myocilin Gene (Myoc) Suggests that Human Glaucoma-Causing Mutations Are Gain of Function", *Molecular and Cellular Biology*, Nov. 2001, vol. 21, No. 22, Copyright © 2001, American Society for Microbiology, pp. 7707-7713.

Joe, M. K. et al., "Accumulation of mutant myocilins in ER leads to ER stress and potential cytotoxicity in human trabecular meshwork cells", *Biochem. and Biophys. Res. Comm.*, 312, Copyright © 2003, Elsevier Inc., pp. 592-600.

Hohjoh, H., "RNA Interference (RNAi) induction with various types of synthetic oligonucleotide duplexes in cultured human cells", *FEBS Letters 521*, © 2002 Published by Elsevier Science B.V. on behalf of the Federation of European Biochemical Societies, pp. 195-199.

Fautsch and Johnson, "Characterization of Myocilin-Myocilin Interactions", *Investigative Ophthalmology & Visual Science*, Sep. 2001, vol. 42, No. 10, Copyright © Association for Research in Vision and Ophthalmology, pp. 2324-2331.

Harris et al., "Expression of caveolin by bovine lymphocytes and antigen-presenting cells", *Immunology 2002*, 105, © 2002 Blackwell Science Ltd., pp. 190-195.

Caballero and Borras. "Inefficient Processing of an Olfactomedin-Deficient Myocilin Mutant: Potential Physiological Relevance to Glaucoma", *Biochemical and Biophysical Research Communications 282*, Copyright © 2001 by Academic Press, pp. 662-670.

Elbashir et al., "Duplexes of 21-nucleotide RNAs mediate RNA interference in cultured mammalian cells", *Nature*, vol. 411, May 24, 2001, © 2001 Macmillan Magazines Ltd., pp. 494-498.

Jacobson et al., "Non-secretion of mutant proteins of the glaucoma gene *myocilin* in cultured trabecular meshwork cells and in aqueous humor", *Human molecular Genetics*, © 2001 Oxford University Press, vol. 10, No. 2, pp. 117-125.

Morcos, "Achieving Efficient Delivery of Morpholino Oligos in Cultured Cells", *Genesis*, 30, 94-102, © 2001 Wiley-Liss, Inc., pp. 94-102.

Fire et al., "Potent and specific genetic interference by double-stranded RNA in *Caenorhabditis elegans*", *Nature*, 1998 © Macmillan Publishers Ltd., vol. 391, pp. 806-811.

Lipardi et al., "RNAi as Random Degradative PCR: siRNA Primers Convert mRNA into dsRNAs that Are Degraded to Generate New siRNAs", *Cell*, vol. 107, Nov. 2, 2001, Copyright © 2001 by Cell Press, pp. 297-307.

www.sciencemag.org, Stone et al., "Identification of a Gene That Causes Primary Open Angle Glaucoma", *Science*, vol. 275 (1997) pp. 668-670.

www.sciencemag.org, Hamilton et al., "A Species of Small Antisense RNA in Posttranscriptional Gene Silencing in Plants", *Science*, vol. 286, Oct. 29, 1999, pp.950-952.

www.sciencemag.org, Brummelkamp et al., "A System for Stable Expression of Short Inerfering RNAs in Mammalian Cells", *Science*, vol. 296, Apr. 19, 2002, pp. 550-553.

\* cited by examiner

| Name | sequence-sense strand | expression (% of control) | residue covered | SEQ ID NO |
|---|---|---|---|---|
| 1. Control | 5'-aacagtcgcgtttgcgactgg-3' | 100% | * | 5 |
| 2. siMYOC-A | 5'-aacttacagagagacagcagc-3' | 13.3+/- 10.9 % | R76 | 1 |
| 3. siMYOC-B | 5'-aataccgagacagtgaaggct-3' | 10.2 +/- 15.3 % | E352 | 2 |
| 4. siMYOC-C | 5'-aacatccgtaagcagtcagtc-3' | 10.5 +/- 14.2 % | K423 | 3 |
| 5. siMYOC-D | 5'-aaccccctggagaagaagctc-3' | 11.3 +/- 9.9 % | N480 | 4 |

*Blast search of the control sequence did not find a similarity to any mammalian gene or to the EGFP cDNA.

METHODS OF TREATING OCULAR CONDITIONS

CROSS-REFERENCE TO RELATED APPLICATIONS

This application is a continuation of International application number PCT/US2005/012607, filed Apr. 13, 2005, which claims priority to U.S. Provisional Application Ser. No. 60/561,779, filed Apr. 13, 2004, the content of which is herein incorporated in its entirety by reference.

STATEMENT REGARDING GOVERNMENT FUNDING

This research was supported in part by the National Eye Institute under grant 1RO3EY016088 and RO1-AR48147. The U.S. government has certain rights in the invention.

BACKGROUND OF THE INVENTION

Glaucoma is one of the leading causes of blindness in the world. It affects approximately 66.8 million people worldwide. At least 12,000 Americans are blinded by this disease each year (Kahn and Milton, 1980). Glaucoma is characterized by the degeneration of axons in the optic nerve head, primarily due to elevated intraocular pressure (IOP). One of the most common forms of glaucoma, known as primary open-angle glaucoma (POAG), results from the increased resistance of aqueous humor outflow in the trabecular meshwork (TM), causing IOP elevation and eventual optic nerve damage.

Recent studies have linked POAG and juvenile open-angle glaucoma (JOAG) to the mutation of myocilin (Tamm et al., 2002; Jacobson et al., 2001). Myocilin, a secretory protein was first identified in cultured human TM cells treated with dexamethasome. In situ hybridization experiments revealed that myocilin is present in many ocular tissues including conjunctiva, sclera, TM and cornea and non-ocular tissues such as smooth muscle. In humans, the gene encoding myocilin is located in chromosome 1 (1q21-q31) and was initially named TIGR (TM-Inducible-Glucocorticoid-Response protein) (Jacobson et al., 2001).

SUMMARY OF THE INVENTION

The present invention provides a method of suppressing the accumulation of myocilin in an ocular tissue cell by introducing a ribonucleic acid (RNA) into the cell in an amount sufficient to suppress accumulation of myocilin, wherein the RNA is a double-stranded molecule with a first strand of RNA that is a ribonucleotide sequence that corresponds to a nucleotide sequence encoding myocilin and a second strand of RNA that is a ribonucleotide sequence that is complementary to the nucleotide sequence encoding myocilin, wherein the first and the second ribonucleotide strands are complementary strands that hybridize to each other to form the double-stranded molecule, and wherein the double-stranded molecule suppresses accumulation of myocilin in the ocular tissue cell. In certain embodiments, the first strand of RNA is SEQ ID NO:1, SEQ ID NO:2, SEQ ID NO:3, or SEQ ID NO:4.

The present invention provides a method of preventing cytotoxic effects of mutant myocilin in an ocular tissue cell by introducing a ribonucleic acid (RNA) into the cell in an amount sufficient to suppress accumulation of myocilin, wherein the RNA is a double-stranded molecule with a first strand of RNA that is a ribonucleotide sequence that corresponds to a nucleotide sequence encoding myocilin and a second strand of RNA that is a ribonucleotide sequence that is complementary to the nucleotide sequence encoding myocilin, wherein the first and the second ribonucleotide strands are complementary strands that hybridize to each other to form the double-stranded molecule, and wherein the double-stranded molecule prevents cytotoxic effects of myocilin in the ocular tissue cell.

The present invention further provides a method to inhibit expression of a myocilin gene in an ocular tissue cell comprising introducing a ribonucleic acid (RNA) into the cell in an amount sufficient to inhibit expression of the myocilin gene, wherein the RNA is a double-stranded molecule with a first strand that is a ribonucleotide sequence that corresponds to a nucleotide sequence of the myocilin gene and a second strand that is a ribonucleotide sequence that is complementary to the nucleotide sequence of the myocilin gene, wherein the first and the second ribonucleotide strands hybridize to each other to form the double-stranded molecule, and wherein the double-stranded molecule inhibits expression of the myocilin gene.

The present invention also provides a method to inhibit expression of a myocilin gene in a mammal involving (a) providing a mammal (such as a human) containing an ocular tissue cell, wherein the myocilin cell contains the myocilin gene and the ocular tissue cell is susceptible to RNA interference, and the myocilin gene is expressed in the ocular tissue cell; (b) contacting the mammal with a ribonucleic acid (RNA), wherein the RNA is a double-stranded molecule with a first strand that is a ribonucleotide sequence that corresponds to a nucleotide sequence of the myocilin gene and a second strand that is a ribonucleotide sequence that is complementary to the nucleotide sequence of the myocilin gene, wherein the first and the second ribonucleotide sequences are complementary strands that hybridize to each other to form the double-stranded molecule, thereby inhibiting expression of the myocilin gene.

In embodiments of the present invention, the accumulation and/or expression of myocilin may be suppressed or inhibited by at least 10%. In embodiments of the present invention, the ocular tissue cell is conjunctiva, sclera, trabecular meshwork (TM) or cornea. In certain embodiments, the ocular tissue is TM, such as human TM. The TM cell that is the subject of the present invention may be located in vivo in a mammal.

The present invention also provides a method of treating glaucoma in a patient in need thereof comprising administering to the patient a ribonucleic acid (RNA) in an amount sufficient to suppress accumulation of myocilin in an ocular tissue cell, wherein the RNA is a double-stranded molecule with a first strand of RNA that is a ribonucleotide sequence that corresponds to a nucleotide sequence encoding myocilin and a second strand of RNA that is a ribonucleotide sequence that is complementary to the nucleotide sequence encoding myocilin, wherein the first and the second ribonucleotide strands are complementary strands that hybridize to each other to form the double-stranded molecule, and wherein the double-stranded molecule suppresses accumulation of myocilin in the ocular tissue cell. In certain embodiments of the present invention, the ocular tissue cell may be conjunctiva, sclera, trabecular meshwork (TM) or cornea. In embodiments of the present invention, the glaucoma is an open-angle glaucoma. In embodiments of the present invention, the expression of myocilin is inhibited by at least 10%.

In embodiments of the described methods of the present invention, the double-stranded ribonucleic acid structure may be, for example, from about 21 to about 23 bases in length and each of the ribonucleic acid strands may able to specifically hybridize to a deoxyribonucleic acid strand of the myocilin gene over the about 21 to about 23 bases. In the method of the present invention, the myocilin may be a mutant myocilin.

The present invention provides a method of making and identifying an isolated myocilin-specific RNA that inhibits myocilin activity in a cell involving (a) generating an RNA that is a double-stranded molecule with a first strand of RNA that is a ribonucleotide sequence that corresponds to a nucleotide sequence encoding myocilin and a second strand of RNA that is a ribonucleotide sequence that is complementary to the nucleotide sequence encoding myocilin, wherein the first and the second ribonucleotide strands are complementary strands that hybridize to each other to form the double-stranded molecule, and wherein the double-stranded molecule suppresses accumulation of myocilin in an ocular tissue cell; and (b) screening the RNA to determine whether the RNA inhibits myocilin activity in a cell. In embodiments of the present invention, the ocular tissue cell is conjunctiva, sclera, trabecular meshwork (TM) or cornea. The myocilin may be inhibited by at least 10%, or may be inhibited by at least 50%, or may be inhibited by at least 80%. In certain embodiments of this invention, the RNA is introduced by topical administration.

The present invention also provides myocilin-specific RNA molecules made by the methods described above. In embodiments of this myocilin-specific RNA, the RNA may include a double-stranded ribonucleic acid structure is from about 21 to about 23 bases in length and each of the ribonucleic acid strands is able to specifically hybridize to a deoxyribonucleic acid strand of the myocilin gene over the at least 21 to 23 bases.

The present invention further provides an isolated myocilin-specific ribonucleic acid (RNA), wherein the RNA is a double-stranded molecule with a first strand of RNA that is a ribonucleotide sequence that corresponds to a nucleotide sequence encoding myocilin and a second strand of RNA that is of a ribonucleotide sequence that is complementary to the nucleotide sequence encoding myocilin, wherein the first and the second ribonucleotide strands are complementary strands that hybridize to each other to form the double-stranded molecule, and wherein the double-stranded molecule suppresses accumulation of myocilin in a trabecular meshwork (TM) cell.

BRIEF DESCRIPTION OF THE FIGURES

FIG. 2 depicts the use of the siFinder program to identify siRNA candidates.

FIG. 5. Suppression efficiency of myocilin-specific siRNAs in HEK293 cell determined from western blotting experiments. Data are from five independent transfection experiments (mean+/−SD, n=5). Results of all four myocilin-specific siRNAs were statistically different from the control siRNA (Student's t-test, p<0.05).

FIG. 6. The suppression of myocilin wild-type ("MYOC-WT") and Q368X ("MYOC-Q368X") proteins by siMYOC-ApH1-RNA in TM5 cells.

DETAILED DESCRIPTION

Myocilin is a secretory protein first identified in cultured human trabecular meshwork (TM) cells treated with dexamethasone. In situ hybridization experiments revealed that myocilin is also present in other ocular tissues including sclera and cornea and in non-ocular tissues such as smooth muscle. In humans, the gene encoding myocilin is located in chromosome 1 (1q21-q31) and it was initially named TIGR (for TM-Inducible-Glucocorticoid-Response protein). Although the function of myocilin is currently unknown, mutations of myocilin have been linked to primary open angle glaucoma (POAG) and juvenile open angle glaucoma (JOAG). It is generally believed that the intracellular accumulation of misfolded mutant myocilins results in TM cell death, which in turn causes obstruction of TM and increased resistance of aqueous outflow. Subsequent elevation of intraocular pressure eventually leads to axon degeneration of the optic nerve and blindness. Currently, 43 myocilin mutations have been associated with JOAG and approximately 3% of POAG patients (for review, see references 5 and 24 by Fingert et al., 2002 and Tamm, 2002).

In the eye, myocilin is expressed in high amounts in the trabecular meshwork (TM), sclera, ciliary body and iris, and at considerable lower amounts in retina and optic nerve head. Secreted myocilin is present in the aqueous humor. In the TM, myocilin is found within the cytoplasm of TM cells and in the juxtacanalicular region in association with fibrillar extracellular matrix components. The Myoc gene has been linked to both the adult- and juvenile-onset open-angle glaucomas (OAG) (Stone et al., 1997; Shimizu et al., 2000).

Figure 1:
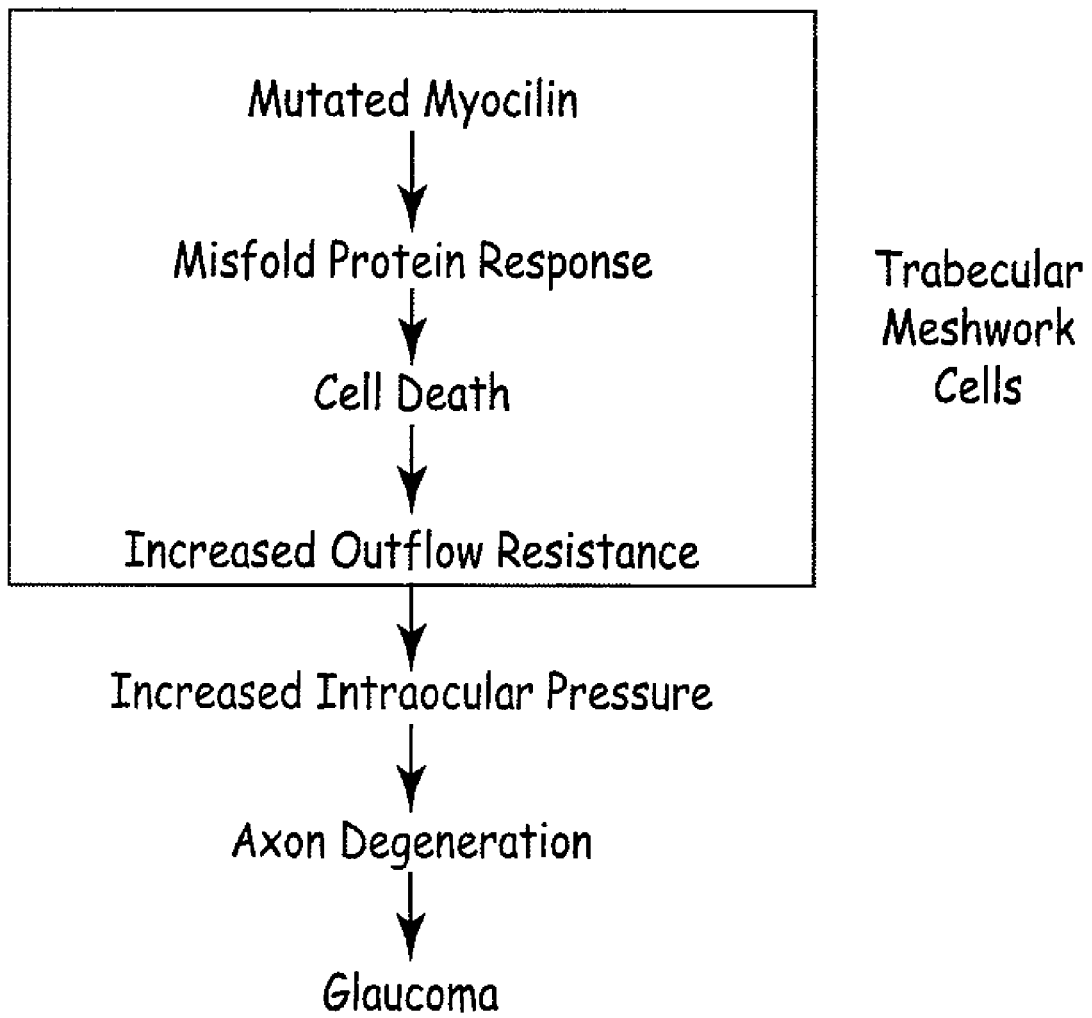
FIG. 1 is a schematic illustration the pathogenesis of myocilin-related glaucoma.

While the actual function of myocilin remains unclear, it is believed that the accumulation of misfolded mutant myocilin proteins induces TM cell death, which causes obstruction of TM and increased resistance of aqueous outflow (Polansky et al., 1984; Sohn et al., 2002). Subsequent elevation of IOP eventually leads to axon degeneration of the optic nerve and blindness (FIG. 1). Genetic linkage analysis has associated myocilin mutations in some POAG and JOAG patients (Jacobson et al., 2001).

RNA interference (RNAi), first discovered in *C. elegans* and plants, is a phenomenon in which a double-stranded RNA molecule induces a sequence-specific expression knockdown of its complementary gene. RNAi serves as a mechanism to regulate the gene expression in non-mammalian organisms. In order to use RNAi for regulation of gene expression in the mammalian system, a method was developed using a small 21-23 nucleotide, double-stranded RNA (named "small interfering RNA", siRNA) as a molecular silencer to knock down gene expression. These short RNAi molecules were extremely effective in mRNA suppression (as low as 0.05 nM needed when tested in Hela cells), and they did not elicit anti-viral responses. Using siRNAs as molecular silencers to suppress the expression of target genes has become an important tool for functional analysis of genes. Promoters of RNA polymerase III, such as human H1-RNA or snU6 RNA promoters have been used to generate hairpin siRNA for a steady expression of siRNA in cultured cells. This makes siRNA-mediated gene therapies possible if combined with high efficiency nucleic acid delivery vehicles.

The present inventors have identified siRNAs capable of suppressing the expression of myocilin and its mutants. Since one of the current hypothesis is that the myocilin-related glaucoma causes the degeneration of TM due to the intracellular accumulation of misfolded myocilins, application of siRNAs that suppress and prevent the cytoplasmic accumulation of misfolded myocilin proteins can potentially ameliorate the adverse consequence, thereby preventing TM cell death, elevated IOP, and the eventual development of glaucoma. The high suppression efficiencies of these identified siRNAs also make them a useful tool to study the in vivo functions of myocilin by the gene knock-down approach.

The present inventors have also discovered that the administration of the siRNAs to an ocular tissue cell leads to the selective reduction of the expression of mutant myocilin proteins in the cell. "Ocular tissue cell" refers to a cell obtained or derived from an ophthalmic source, e.g., a cell of the trabecular meshwork (TM) of the eye. Additional types of ocular tissue cells are known in the art. These ocular tissue cells include, but are not limited to, cells from the conjunctiva, sclera, cornea, retina, ciliary body, iris and optic nerve head.

In one embodiment, the siRNAs of the present invention are administered to a patient to treat or prevent an ocular condition. An "ocular condition" is meant to refer to a disease, disorder and/or pathology that is associated with an elevated intraocular pressure. For example, ocular conditions such as glaucoma, proliferative vitreoretinopathy, diabetic retinopathy, uveitis, keratitis, cytomegalovirus retinitis and corneal dystrophies can be treated or prevented by the methods of the present invention. "Treating" as used herein refers to ameliorating at least one symptom of, curing and/or preventing the development of a disease or a condition.

In another embodiment of the invention, siRNAs are employed to inhibit expression of a myocilin gene. By "inhibit expression" is meant to reduce, diminish or suppress expression of a target gene by any method known to the art. For example, in one embodiment of the invention expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when siRNA initiates the degradation of the mRNA transcribed from a gene of interest in a sequence-specific manner via RNA interference, thereby preventing translation of the gene's product (for a review, see Brantl, 2002).

I. Small Interfering RNA (siRNA)

A "small interfering RNA" or "short interfering RNA" or "siRNA" or "short hairpin RNA" or "shRNA" is a RNA duplex of nucleotides that is targeted to a gene interest, for example, Myoc. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding myosin or sequences encoding olfactomedin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. In certain embodiments, the loop is 9 nucleotides in length. The hairpin structure can also contain 3' or 5' overhang portions. In some embodiments, the overhang is a 3' or a 5' overhang 0, 1, 2, 3, 4 or 5 nucleotides in length.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of myocilin may be reduced by 10, 20, 30, 40, 50, 60, 70, 80, 90, 95, or 99%. In some embodiments, the expression is reduced by about 90% (i.e., only about 10% of the amount of myocilin is observed a cell as compared to a cell where siRNA molecules have not been administered). Knock-down of gene expression can be directed by the use of dsRNAs or siRNAs. For example, "RNA interference (RNAi)," which can involve the use of siRNA, has been successfully applied to knockdown the expression of specific genes in plants, *D. melanogaster, C. elegans*, trypanosomes, planaria, hydra, and several vertebrate species including the mouse. For a review of the mechanisms proposed to mediate RNAi, please refer to Bass et al., 2001, Elbashir et al., 2001 or Brantl, 2002.

According to a method of the present invention, the expression of myocilin can be modified via RNAi. For example, the accumulation of myocilin can be suppressed in an ocular tissue cell. The term "suppressing" refers to the diminution, reduction or elimination in the number or amount of transcripts present in a particular cell. For example, the accumulation of mRNA encoding myocilin can be suppressed in an ocular tissue cell by RNA interference (RNAi), e.g., the Myoc gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

The terms "myocilin," "wild-type myocilin" and "native myocilin" are meant to refer to a secreted 55-57 kDa glycoprotein protein (e.g., BAA24532) that is encoded by the gene Myoc (e.g., BC029261), which is also referred to in the literature as the trabecular meshwork-inducible glucocorticoid response gene (TIGR). Myocilin forms dimers and multimers, and has characteristic structural motifs including a myosin-like domain, a leucine zipper region and an olfactomedin domain. For example, the human mycocilin gene contains 3 exons, encoding a 504-amino acid protein with an N-terminal myosin-like domain that includes a leucine zipper motif, and a C-terminal olfactomedin-like domain. In certain embodiments, the siRNAs target the sequences encoding myocin or olfactomedin. (See, e.g., FIG. 3)

A "mutant myocilin" refers to the protein encoded by a Myoc gene having a mutation, e.g., a missense or nonsense mutation in one or both alleles of Myoc, such as may occur at the GLC1A locus of chromosome 1q21-q31. In addition, mutations in Myoc have been identified in patients with POAG are localized in the olfactomedin domain, which is highly conserved among species. A mutant myocilin may be disease-causing, i.e., may lead to a disease associated with elevation of intraocular pressure (IOP), such as glaucoma, in an animal having either one or two mutant allele(s).

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of an regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995). "3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the world wide web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. See the world wide web at ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell, infra, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the $T_m$ for a particular nucleic acid molecule.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

II. RNA Interference and the Suppression of Genes in Ocular Tissue Cells.

RNA interference (RNAi) is the process of targeted gene silencing, wherein sequence-specific, post-transcriptional gene silencing is initiated by siRNA. RNAi represents a conserved regulatory motif, and is believed to be involved in anti-viral defense, modulation of transposon activity, and regulation of gene expression. RNAi was first discovered in C. elegans and plants (Wiggs and Vollrath, 2001; Fire et al., 1998). It is a phenomenon in which a double-stranded RNA molecule (dsRNA) induces a sequence-specific expression knock-down of its complementary gene. RNAi serves as a mechanism to regulate the gene expression in non-mammalian organisms (Hamilton and Baulcombe, 1999). In order to apply RNAi to a mammalian system for regulation of gene expression, a method has been developed utilizing a small 21-23 nucleotide, double-stranded RNA (named "small interfering RNA" or "siRNA") as a molecular silencer to knock-down gene expression (Hamilton and Baulcombe, 1999). The short RNAs have been shown by many researchers to be effective in mRNA suppression (as little as 0.05 nM is needed when tested in Hela cells) and they did not elicit anti-viral responses (Hamilton and Baulcombe, 1999; Elbashire et al., 2001; Brummelkamp et al., 2002; Yu et al., 2002).

Recently it has been shown that endogenously encoded triggers of gene silencing act through elements of the RNAi machinery to regulate the expression of protein-coding genes. These small temporal RNAs (stRNAs) are transcribed as short hairpin precursors (~70 nt), processed into active, 21-nt RNAs by Dicer, and recognize target mRNAs via base-pairing interactions (Paddison et al., 2002). In addition, short hairpin RNAs (shRNAs) can be engineered to suppress the expression of a gene of interest.

siRNA-mediated gene suppression is specific. Several groups have reported that even a single base pair mismatch between siRNA and the targeted gene could abolish the action of RNA interference (Yu et al., 2002). In addition, the effect of RNAi can last up to 72 hours (Elbashire et al., 2001).

A. Nucleic Acid Molecules of the Invention

Sources of nucleotide sequences from which the present nucleic acid molecules can be obtained include any vertebrate, such as a mammalian, cellular source.

As discussed above, the term "isolated nucleic acid" refers to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule that is transcribed into an siRNA. Such an isolated siRNA may, for example, form a hairpin structure with a duplex 21 base pairs in length that is complementary or hybridizes to a sequence in a gene of interest, and remains stably bound under stringent conditions (as defined by methods well known in the art). Thus, the RNA or DNA is "isolated" in that it is free from at least one contaminating nucleic acid with which it is normally associated in the natural source of the RNA or DNA and in one embodiment of the invention is substantially free of any other mammalian RNA or DNA.

In addition to a DNA sequence encoding a siRNA, the nucleic acid molecules of the invention include double-stranded interfering RNA molecules, which are useful to inhibit expression of a target gene.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. This technique is known in the art. Briefly, nucleic acid encoding a siRNA can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding siRNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such.

The DNA template can be generated by those vectors that are either derived from bacteriophage M13 vectors (the commercially available M13mp18 and M13mp19 vectors are suitable), or those vectors that contain a single-stranded phage origin of replication. Thus, the DNA that is to be mutated may be inserted into one of these vectors to generate single-stranded template. Production of the single-stranded template is described in Chapter 3 of Sambrook and Russell, 2001. Alternatively, single-stranded DNA template may be generated by denaturing double-stranded plasmid (or other) DNA using standard techniques.

B. Identification of siRNA Target Sequences

There are well-established criteria for designing siRNAs (see, e.g., Elbashire et al., 2001). Details can be found in the websites of several commercial vendors such as Ambion, Dharmacon and Oligoengine. However, since the mechanism for siRNAs suppressing gene expression is not entirely understood and siRNAs selected from different regions of the same gene do not work as equally effective, very often a number of siRNAs have to be generated at the same time in order to compare their effectiveness.

The present inventors developed an in-house, web-based program, SiFinder, which can be found on the world-wide-web at ahc.umn.edulcgi-bin/CorneaLab/SiFinder.cgi, to design myocilin-specific siRNAs Below is a short description of the SiFinder software:

1. Input of Interested Gene

The inventors input the cDNA sequence for myocilin into the sequence box (FIG. 1A). The program searched for any AA dinucleotide plus 19 nucleotides downstream as potential siRNA targeting candidates (FIG. 1B). For designing hairpin siRNA, longer length (up to 29 nucleotide duplex) was reported to be more effective (Paddison et al., 2002) as the longer sequence might improve the processing of hairpin siRNA by Dicer. Next, the inventors selected that the GC content of the siRNA candidates to be displayed must be between 45 to 70%. Higher GC content can impair the siRNA efficiency and make the sequence confirmation by standard automated sequencing method difficult in some cases. Further parameters were chosen, namely, that there could not be five consecutive Ts in the sense or antisense region. The last nucleotide cannot be a T (or the first nucleotide after AA cannot be an A), since this would result in an early termination of the transcription by RNA polymerase III. It was also checked to verify that there was no internal secondary structure. The selected candidate sequences for potential siRNAs were then checked for any possible match with other genes or polymorphism of the target gene by Blast search. In SiFinder, submission of the potential siRNA candidates for Blast search is enabled by the button of "Search at Blast!" underlying each sequence. Once confirmed by Blast search that there are no other genes which match with the sequence of candidate siRNA (so that other genes would not be suppressed), two strategies could be chosen to produce siRNA: either synthetic siRNA by custom synthesis, or hairpin siRNA generated by plasmids containing RNA polymerase III promoter. The hairpin or spacer sequence was used as previously described ("TTCAAGAGA" (SEQ ID NO: 14) as default for pH1-RNA) (Brummelkamp 2002).

2. Generation of Synthetic siRNA Molecule

Figure 2:
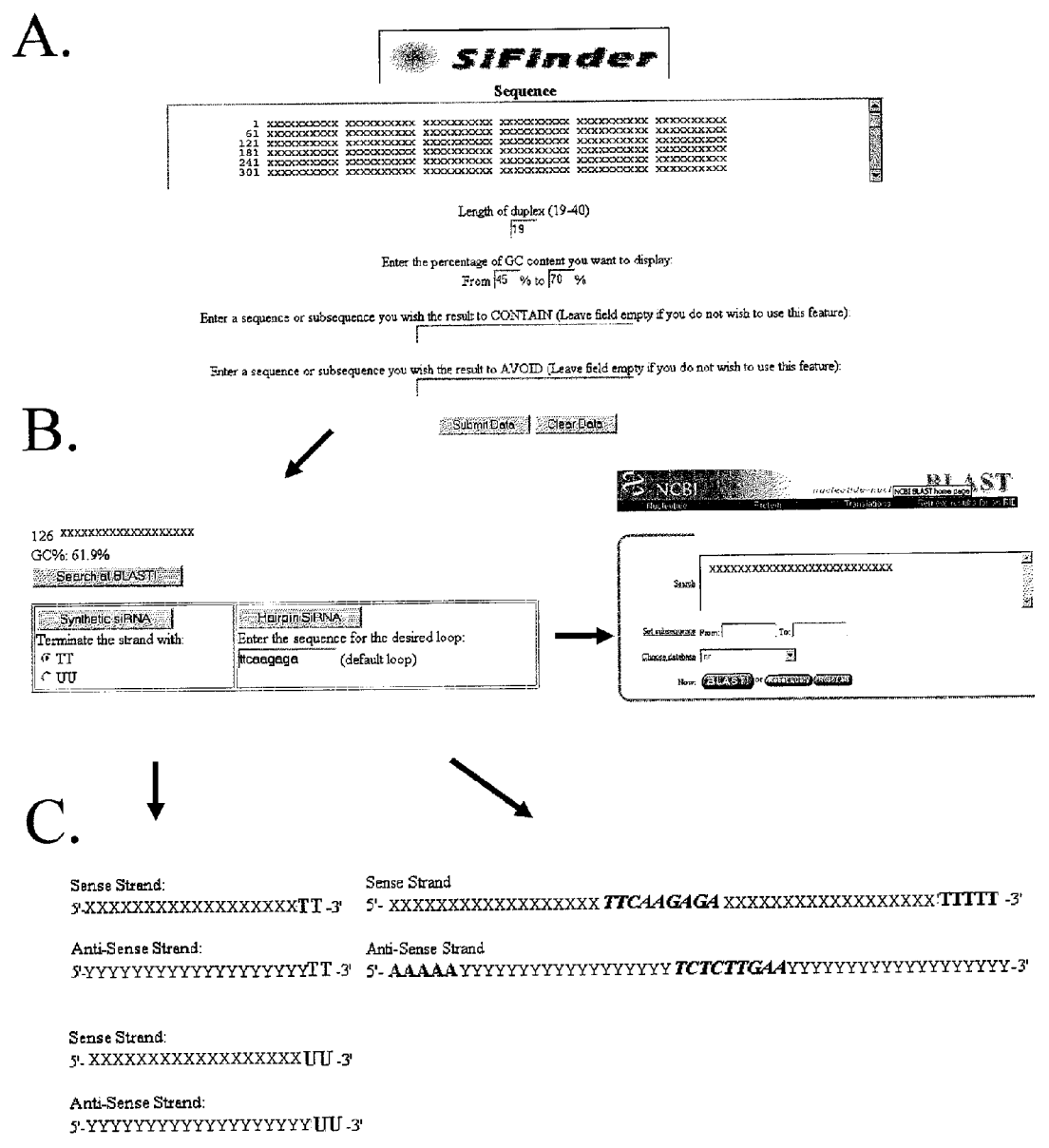

When synthetic siRNAs were made, one can choose to have TT or UU overhang at the 3' end (FIG. 2C). A TT overhang is more commonly used as the obvious benefit is to reduce the potential RNase degradation. Some vendors also suggest that using UU overhang at the 3' end can lead to lower yield for synthesized product. However, recent report by Hohjoh (Hohjoh et al., 2002) suggests that UU 3'-overhangs rather than TT could induce more efficient RNAi activity for synthetic siRNA when transfected into human cells.

3. Generation of Stem-Loop DNA Oligonucleotides for siRNA Expression by H1-RNA or snU6 RNA Promoter For generating hairpin siRNA in host cells, various vectors have been constructed (FIG. 2C) utilizing either H1-RNA or snU6 RNA promoter. A 3-9 nucleotide loop was inserted between sense and antisense strands for forming a hairpin RNA molecule when transcribed by RNA polymerase III. The default sequence for the loop was "TTCAGAAGG" (SEQ ID NO: 15) as used in a previous report (Brummelkamp et al., 2002). However, other user-defined loop sequences could be input to generate desired loop. A TTTTT (SEQ ID NO:16) penta-nucleotide is automatically attached to the end of antisense strand and serves as a terminator for RNA polymerase III transcription. siRNA candidates that contain more than three consecutive Ts should be avoided since RNA polymerase III will terminate the transcription if the DNA template contains four or more consecutive Ts.

The promoter of H1-RNA was synthesized and ligated into a pBluescript KS(+)II. The sense and antisense oligo sequences are as below:

```
H1-RNA-P.5
5'-taatatttgcatgt cgctatgtgt      (SEQ ID NO: 12)
tctgggaaat caccataaac gtgaaatgtc
tttggatttg ggaatcttat aagttctgta
tgagaccact ctttcccgggc-3'

H1-RNA-P.3
5'-tcgagcccgggaaagagtggtctcataca  (SEQ ID NO: 13)
gaacttataagattcccaaatccaaagacatt
tcacgtttatggtgatttcccagaacacatag
cgacatgcaaatat-3'
```

The inventors also used pSuper from Oligoengines Ltd which has the same motif/promoter to perform the siRNA construction.

C. Generation of siRNAs of the Invention

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

In addition, siRNAs can be prepared in vivo, for example, in cultured cells (see, for example, Elbashir et al., 2001; Brummelkamp et al., 2002; and Lee et al., 2002). To prepare expression cassettes for the recombinant production of an siRNA of the invention, a recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein. For example, Sambrook and Russell, infra, provides suitable methods of construction.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a DNA into a host cell include calcium phosphate precipitation, lipofection, particle bombardment, microinjection, electroporation, and the like. Biological methods to introduce the DNA of interest into a host cell include the use of DNA and RNA viral vectors.

A "transfected" or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

As described herein, an expression cassette of the invention contains, inter alia, a promoter. Such promoters include the H1-RNA or CMV promoter, as well as the RSV promoter, SV40 late promoter and retroviral LTRs (long terminal repeat elements).

In one embodiment of the present invention, an expression cassette may contain an H1-RNA promoter that is operably linked to a nucleic acid sequence encoding a siRNA. Thus, the H1-RNA promoter initiates the transcription of the siRNA. In another embodiment, the promoter is regulatable, providing inducible expression of the siRNA.

III. Diseases and Conditions Amenable to the Methods of the Invention

The term glaucoma refers to a heterogeneous eye disease that can lead to damage to the eye's optic nerve and result in blindness. The term includes open-angle glaucoma (OAG) such as primary open-angle glaucoma (POAG) and juvenile open-angle glaucoma (JOAG), low-tension or normal-tension glaucoma, closed-angle glaucoma, congenital glaucoma, secondary glaucoma, pigmentary glaucoma, and neovascular glaucoma.

Recent studies have linked the mutations of myocilin to the pathogenesis of glaucoma in certain patients (Jacobson et al., 2001; Polansky et al., 1979). Myocilin is an extracellular protein secreted by many types of cells. Several researchers have suggested that the misfolded proteins of mutant myocilin cannot be secreted by trabecular meshwork (TM) cells (Polansky et al., 1979; Polansky et al., 1984)). It is believed that intracellular accumulation of mutant myocilin results in cytotoxic effects and cell death in TM, and contributes to at least two types of open-angle glaucoma (FIG. 1). Suppressing the accumulation of mutant myocilin proteins in TM cells can prevent the cytotoxic effects, cell death, and may mitigate myocilin-related open-angle glaucoma. RNA interference (RNAi) technologies are used to modulate, e.g., suppress, the expression of wild-type and mutant myocilin proteins in cultured TM cells.

The pathogenesis for genetic diseases is due to one of the two mechanisms: (1) gain-of-function (mutant protein generates cytotoxic effect) or (2) loss-of-function or haloinsufficiency (only half of the amount of the protein is produced and fails to achieve its proper function). There is strong evidence indicating that the myocilin-related glaucoma is due to the gain-of-function mechanism rather than loss-of-function.

When cDNAs encoding mutant myocilin were transfected into cultured TM cells, the expressed mutant myocilin proteins formed aggregates of misfolded proteins inside the TM cells and failed to be secreted extracellularly. The presence of the misfolded proteins was evidenced by overexpression of β-crystallin in myocilin-related glaucoma patients and co-localization of protein disulfide isomerase (PDI) with aggregated mutant myocilin in ER. The mutant myocilins also prevented the secretion of wild-type protein when cDNAs of both wild-type and mutant myocilins were co-transfected into cultured TM cells (Polansky et al., 1979)). Since there is direct evidence suggesting that myocilin forms dimers or even oligomers in vivo (Caballero and Borras, 2001), it is likely that misfolded mutant myocilins bind and "trap" wild-type proteins inside the cells. It has also been shown that expression of mutant myocilin causes significant cell death in cultured TM cells (Polansky et al., 1984). Loss of TM cells in aged and glaucomatous animals correlates well with increased resistance of aqueous humor outflow and elevated IOP (Sohn et al., 2002). Taken together, these data suggest that mutant myocilins are likely to cause cytotoxic effects and cell death.

Myocilin-knockout experiments revealed no discernable phenotype and normal IOP in myocilin-null animals (Ortego et al., 1997). Patients with deletion of myocilin gene also did not develop glaucoma (Russell et al., 2001). For patients carrying an Arg46Stop mutation (which results in a severely truncated form of myocilin, missing more than 90% of the amino acid residues of the wild-type protein), all but one homozygous or heterozygous patients have no evidence of glaucoma (Fautsch and Johnson, 2001; Kim et al., 2001). It was estimated that 3% of the Asian control subjects (non glaucomatous) carry this Arg46Stop mutation (Kim et al., 2001). Therefore, the Arg46Stop mutation is considered a polymorphism rather than a glaucoma-causing mutation (Kim et al., 2001).

The fact that patients with the deleted myocilin gene or with the Arg46Stop mutation remain asymptomatic supports the notion that loss of wild-type myocilin does not result in disease manifestation. Instead, the glaucoma conditions caused by myocilin mutation in humans are likely mediated through a gain-of-function mechanism, due to the cytotoxic effect and subsequent cell death caused by mutant myocilin proteins.

IV. Therapeutic Agents of the Invention

The siRNAs of the present invention are administered in a number of ways. For example, the nucleic acid encoding the siRNA can be contained in a viral vector, a nanoparticle (also called nanoencapsulated particles or nanocapsules) or a liposome. Nanocapsules can be produced using known methods. See, e.g., PCT/US03/10729, PCT/US03/10854, PCT/US03/10850, and WO00164164.

In one embodiment, the sequence encoding the siRNA-generating element of pH1-RNA is cloned into a lentivirus (e.g., pLenti6-V5, Invitrogen). Virus particles will then be produced by infecting cultured 293 FT cells. In a nanoparticle embodiment, the pH1-RNA is nanoencapsulated particles. For example, the nucleic acid is condensed into a sub-50 nanometer size with RGD-peptide coating. The viral vectors or nanoparticles are administered to the TM cells (e.g., TM5 cells).

In addition to administering siRNA to a patient, active agents which may find use in the present invention to treat an ocular condition include, but are not limited to, the following therapeutic classes: Ace-inhibitor; endogenous cytokines that influence basement membrane; agents that influence growth of endothelial cells; adrenergic agonist or blocker; aldose reductose inhibitor; analgesic; anesthetic; antiallergic; antibacterial; antifibrotic; antifungal, e.g. amphoteracin B; anti-glaucoma; antihyper- or hypotensive; anti-inflammatory; antineoplastic; antiprotozoal; antitumor; antimetabolites, e.g., folic acid analogs, purine analogs, and pyrimidine analogs; antiviral; carbonic anhydrase inhibitor; chelating agents; cholinergic; cholinesterase inhibitor; dopamine receptor agonist or antagonist; estrogen; glucocorticoid; glucosidase inhibitor; releasing factor; growth hormone inhibitor; growth stimulant; hemolytic; heparin antagonist; immunomodulator; immunosuppressant; LH-RH agonist; antimitotics; NSAID; anti-glaucoma agents, e.g. acetozolamide (dimox), befunolol, beta-blockers, Ca-blockers, etc.; anti-neoplastics, e.g., vinblastine, vincristine, interferons alpha, beta, and gamma; progesterone; thrombolytic; vasodilator; vasopressor; and vitamin.

Among hydrophobic drugs, which typically have a slow release profile and therefore benefit from formulation with a release accelerator, are cyclosporines, e.g. cyclosporin A, cyclosporin G, etc.; vinca alkaloids, e.g. vincristine and vinblastine; methotrexate; retinoic acid; certain antibiotics, e.g. ansamycins such as rifampin; nitrofurans such as nifuroxazide; non-steroidal anti-inflammatory drugs, e.g. diclofenac, keterolac, flurbiprofen, naproxen, suprofen, ibuprofen, aspirin; etc. Steroids are of specific interest, in particular steroidal compounds with anti-inflammatory activity, i.e. glucocorticoids.

V. Dosages, Formulations and Routes of Administration of the Agents of the Invention The agents of the invention are preferably administered so as to result in a reduction in at least one symptom associated with an ocular condition and/or disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

Administration of siRNA may be accomplished through the administration of the nucleic acid molecule itself, or by administering a nucleic acid molecule encoding the siRNA (see, for example, Felgner et al., U.S. Pat. No. 5,580,859, Pardoll et al., 1995). Pharmaceutical formulations, dosages and routes of administration for nucleic acids are generally disclosed, for example, in Felgner et al., supra.

The present invention envisions treating an ocular disease, for example, glaucoma, in a mammal by the administration of an agent, e.g., a nucleic acid composition.

Administration of the therapeutic agents in accordance with the present invention may be continuous or intermittent, depending, for example, upon the recipient's physiological condition, whether the purpose of the administration is therapeutic or prophylactic, and other factors known to skilled ophthalmologists. The administration of the agents of the invention may be essentially continuous over a preselected period of time or may be in a series of spaced doses. The siRNA of the present invention would be administered locally, such as topically.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091), can be administered by a variety of routes, including by direct administration into the diseased tissue. For example, the therapeutic agent may be introduced directly into the ocular tissue of interest via an eye drop, ointment or spray.

The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for administration. The pharmaceutical formulations of the therapeutic agents of the invention can also take the form of an aqueous or anhydrous solution or dispersion, or alternatively in the form of an emulsion or suspension.

Thus, the therapeutic agent may be formulated for administration and may be presented in unit dose form in ampules, pre-filled applicators, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Examples.

Example 1

Suppression of Myocilin Expression by Small Interfering RNAs

A. Materials and Methods
1. Suppression of Mutant Myocilin in TM Cells

Figure 3:
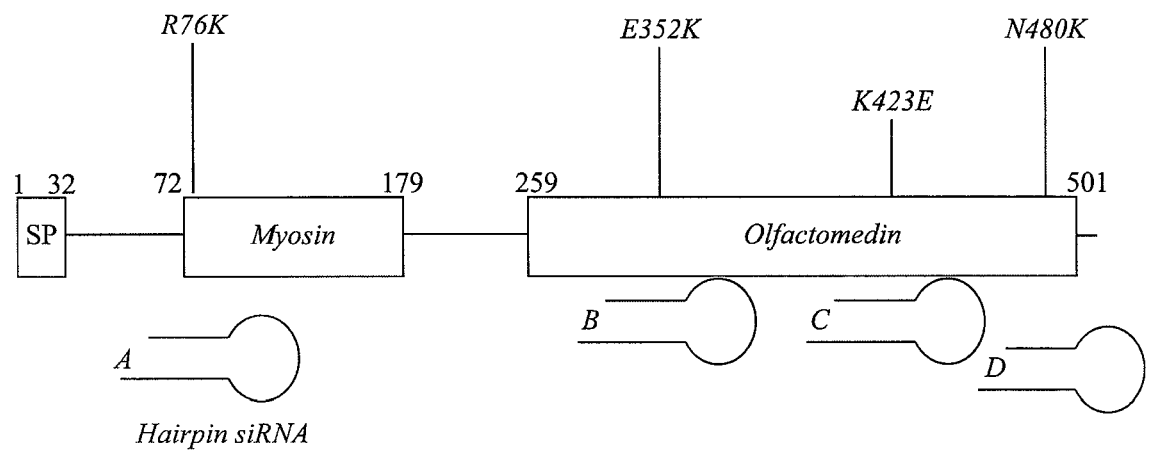
FIG. 3. Myocilin-specific hairpin siRNAs target regions containing residues R76, E352, K423 and N480. siRNAs selected by SiFinder were generated for producing hairpin siRNA in vivo. Mutations of these amino acid residues have been associated with myocilin-related glaucoma. SP: signal peptide; myosin, myosin-like domain; olfactomedin: olfactomedin-like domain.

Disease-causing myocilin mutants were created following the protocol of FIG. 3. These mutants were R76K, E352K, K423E and N480K. The mutation-specific siRNA are used to selectively reduce the expression of mutant myocilins in HEK 293 cells.

The expression of myocilin was suppressed with siRNAs in cultured TM cells and the mammalian cell line HEK 293. Whether the cell death of TM cells induced by mutant myocilins can be rescued by siRNA-mediated suppression is determined. Sohn et al. reported that the truncated myocilin mutant Q368Stop induced cytopathic effect in cultured TM cells (Sohn et al., 2002). The cell proliferation assay is performed on cultured TM cells that are co-transfected with a mutant myocilin plasmid, control plasmid, and/or siMYO-CpH1 to suppress the expression of mutant myocilin (and therefore reduce the cytotoxic effect and cell death).

(a) Plasmid Construction

Oligonucleotides containing the sequence of Human H1 RNA promoter were synthesized by the Microchemical facilities at University of Minnesota. The annealed cassette was inserted into pBlueScript KS(+)II via BamH I and EcoR I sites. The resulting plasmid is named "pH 1-RNA" (Brummelkamp 2002). It was further digested by Bgl II and Hind III and gel-purified.

Two complementary oligonucleotide strands selected by SiFinder containing the myocilin-specific sequence, hairpin loop and pentathymidine terminator for generation of siRNA in vivo, were synthesized and cloned into the prepared vector arm of pH 1-RNA. A control plasmid was also generated for internal control by using a 21 nt sequence (5'-aa-cagtcgcgtttgcgactgg-3' (SEQ ID NO:17)), which does not match any known gene sequence in mammalian cells by Blast search.

The cDNA of human myocilin gene was PCR-amplified from an I.M.A.G.E. clone (the I.M.A.G.E. clone of human myocilin was purchased from ResGen (Huntsville, Ala.; clone ID: 5179076). The PCR-amplified full-length myocilin cDNA was subcloned into pEGFP-N1 (Clontech, Palo Alto, Calif.) to generate plasmids that produce the myocilin-EGFP fusion protein construct in mammalian cells (MYOCpEGFP) (primer sequences: HMYOC-BamHI.3: 5'-ggctggatccatcttg-gagagcttgatg-3' (SEQ ID NO:18), and HMYOC-EcoRI.5: 5'-gaagaattcatgaggttcttctgtgcac-3' (SEQ ID NO:19)). The truncated myocilin mutant Q368X was generated by PCR-amplification of cDNA fragment containing amino acid residues 1 to 367 and was then fused with the EGFP gene. The specific sequences were further confirmed by automated sequencing in the Microchemical facilities at University of Minnesota.

The following is the general procedure used to prepare the siRNA used by the present inventors. First, the oligonucleotide was resuspended at 100 pmoles/μl with 10 mM Tris, pH 7.4. The sample was vortexed and incubated at 37° C. for 10 minutes. (For example, 42.70 nmol was resuspended in 427 μl 10 mM Tris pH7.4.) Second, 20 μl of sense oligo was mixed with 20 μl of the matching antisense oligonucleotide in 160 μl of annealing buffer. The annealing buffer contained the following:

10 mM Tris, pH 7.4
50 mM NaCl
5 mM MgSO4 or MgCL2 10 pmoles/λ final concentration Third, the solution was incubated at 100° C. for 10 minutes in a heating block to generate the annealed oligo. The heating block was then allowed to cool off slowly at room temperature. Next, the following ligation reaction was prepared:

| | |
|---|---|
| 1 μl | plasmid digested with Bgl II/Hind III |
| 6 μl | annealed oligo |
| 2 μl | 5× T4 ligase buffer |
| 1 μl | T4 ligase |
| 10 μl or | TOTAL |
| 2 μl | plasmid digested with Bgl II/Hind III |
| 9 μl | annealed oligo |
| 3 μl | 5× T4 ligase buffer |
| 1 μl | T4 ligase |
| 15 μl | TOTAL |

The reaction mixtures were vortexed, spun, and then incubated at 37° C. for 30-60 minutes. After the incubation step, 2

μl 10×RE buffer 3 (New England Biolabs), 8 μl H2O (3 μl if ligation volume was 15 μl) and 0.2 μl Bgl II (if used plasmid digested with Bgl II) was added to each tube (can mix it all together and then aliquot into ligation tubes). For SiMYOC pCMV, Cla I was used. Reaction mixtures were incubated at 37° C. for one hour.

Last, the entire 20 μl reaction mixture was used to transform E. Coli strain XL-1B (200 μl). The transformed cells were then plated.

One resulting plasmid was named MYOCpEGFP. siRNA candidates specific for human myocilin were selected by using the SiFinder program as described herein. The sense and antisense strands of each siRNA were synthesized, annealed and ligated into pH1-siRNA plasmids (named siMYOCpH1). A control plasmid that generates an siRNA that does not have sequence similarity to any mammalian genes (sense strand: 5'-aacagtcgcgtttgcgactgg-3' (SEQ ID NO:5); used by Dharmacon, Inc.) was also constructed to serve as the negative control. The sequence of all clones was confirmed by standard automated sequencing methods. Four siRNAs targeting the mutation hot spots of myocilin associated with POAG and JOAG have been generated, as shown in FIG. 3.

(b) Cell Culture

HEK 293 cells were purchased from American Type Culture Collection (ATCC, Manassas, Va.) and maintained in DMEM/F12 culture medium (Invitrogen, Carlsbad, Calif.) with the addition of 10% fetal bovine serum (FBS, HyClone Laboratories, Logan, Utah) and antibiotics at 5% CO2/humid atmosphere. TM5 cells were maintained in DMEM medium, 10% FBS without sodium pyruvate. The media were replenished every other day and cells were split twice weekly.

(c) Transfection of Cultured Cells

To evaluate the potency of each siRNA in suppressing the expression of MYOC-EGFP, HEK293 cells were seeded into 60-mm culture dishes and grown to about 70 to 90% confluency and both MYOCpEGFP and siRNA-generating plasmids were co-transfected into HEK293 cells. pCMV-βgal (Invitrogen) was also included in transfection mixtures as an internal control to assure consistent transfection efficiency. Transfections of HEK293 cells were performed with Lipofectamine (Invitrogen) per the manufacturer's instructions. For each 60 mm dish, 0.05 μg MYOCpEGFP was co-transfected with 0.1ug pCMV-βgal and 1.0 μg of selected siMYOCpH1-RNA in 2 ml of Opti-MEM. After 4 hours of incubation at 37° C., 2 ml of serum-containing growth medium was added back to each plate. The medium was completely replaced in the next morning with fresh, serum-containing growth medium. The expression of MYOC-EGFP fusion proteins was evaluated by the fluorescence of EGFP at 48 hours after transfection with an Axiovert 200 fluorescence microscope (Zeiss, Thornwood, N.Y.).

As Lipofectamine caused significant cell death in TM5 cell line, transfections of this cell line were performed with Fugene 6 (Roche, Applied Science, Indianapolis, Ind.). TM5 cells were seeded into 6-well plates at 50% confluency 24 hours before transfection. 0.5 μg of siMYOCpH1-RNA were mixed with 0.025 μg MYOCpEGFP and 0.05 μg pCMV-βgal and then added into 97 μl of OptiMem and 5 μl of Fugene 6. After incubation at room temperature for 20 minutes, the mixtures were added into cultured cells and incubated for 24 hours. The medium was completely replaced with fresh medium at 24 hours after transfection. Cells were harvested and evaluated in the same way as the HEK293 cells.

(d) Determination of the Activity of β-galactosidase

The activities of β-galactosidase as an internal standard as mentioned above were measured with the Luminescent β-gal detection kit (Clontech) in the Lumat LB 9507 Luminometer (Berthold Technologies USA, Oak Ridge, Tenn.) according to the manufacturer's instructions. Only transfection experiments with a variation of less than 10% of β-galactosidase activity were included for analysis (e) Western Blots to Evaluate the Suppression of Myocilin Cultured cells were harvested at 48 hours after transfection. After being rinsed with 1×PBS and trypsinization, a fraction of the cells was removed to determine the activity of β-galactosidase, and the remaining cells were extracted with lysis buffer (1% SDS/1×PBS) to prepare lysates for Western blots. Protein concentrations of cell lysates were determined using a BCA Protein Assay Kit (Pierce, Rockford, Ill.). Equal amounts of protein (10-20 μg/lane) from each cell lysate were subjected to electrophoresis on 12% SDS-PAGE gels, and the gels were blotted onto nitrocellulose membranes. The MYOC-EGFP fusion proteins were detected with a mouse anti-EGFP monoclonal antibody (Clontech, Palo Alto, Calif.) at 1:1000 dilutions, followed by a goat anti-mouse secondary antibody conjugated with alkaline phosphatase (Sigma, St. Louis, Mo.) at 1:1000 dilutions. The same membranes were also probed with a mouse anti-β-actin antibody (Sigma) to assure equal loadings of lysates. A BCIP/NBT-blue substrate system (Sigma) was used to visualize the immunoblots, and the membranes were then scanned and digitized with a flatbed scanner. Quantification of myocilins and β-actin was performed with UN-SCAN-IT software (Silk Scientific, Orem, Utah). The pixel intensities from the bands detected by the anti-EGFP antibody were normalized to the pixel intensities from the bands detected by anti-β-actin. The ratios of intensity between the control siRNA and tested siRNAs were used to determine the suppression efficiency of each siRNA.

(f) Luciferase Assay

To evaluate the protein misfolding response and ER stress caused by the accumulation of mutant myocilins, the inventors also investigated the activation of BiP gene by mutant myocilins using luciferase reporter assays (Dual Luciferase Reporter System, Promega, Madison, Wis.). The BiPpGL3 was a gift from Dr. C.D. Chen (Boston University, Boston, Mass.) that contains the rat grp78 (BiP) promoter region −457 to −39 bp constructed as described in previous reports (Szczesna-Skorupa 2004). TM5 cells were harvested at 48 hours after co-transfection with siMYOCpH1-RNA, myocilin-EGFP plasmids, BiPpGL3 and pRL. After aspirating the media and washing cells with 1 ml of 1×PBS, cells were lysed by adding 100 μl of 1× passive lysis buffer (Promega) to each well of the 24-well plates, and the culture plates were gently shaken on a rotating platform for 15 min at room temperature. Twenty microliters of the above lysate was used to measure the luciferase activities with a luminometer as mentioned above. The expressions of firefly (pGL3) and Renilla (pRL) luciferase were measured sequentially for each sample, and the BiP promoter activity was derived from the ratio of firefly luciferase to Renilla luciferase.

(g) Statistical Analysis

Student's t-test was used to determine the significance of the differences in the band intensities of myocilin and β-actin and luciferase assays between control and myocilin-specific siRNAs. $P<0.05$ was considered to indicate a significant between these groups.

(h) Explant Culture of Trabecular Meshwork Cells

Human donor corneas were obtained from Minnesota Lions Eye Bank within 24 hours of death. The human TM explant cultures were prepared as described (Polansky et al., 1979, 1984). Cells from seventh passage were maintained in DME (Dulbecco's modified Eagle medium), 15% FBS, 1 ng/ml FGF-2 (fibroblast growth factor-2) plus antibiotics.

B. Results

The inventors used the web-based program, SiFinder, described above, to search for possible siRNA candidates from targeted gene sequences. SiFinder calculated the GC content, selected optimal sequences for hairpin siRNAs and submitted them to a BLAST search. From the published coding sequence of human myocilin, 102 siRNA candidates were initially identified by the SiFinder program. Candidate siRNAs with sequences covering residues R76, E352, K423 and N480 were chosen to test their suppression efficiencies, as the mutations of these residues have been reported to be associated with POAG. Blast searching revealed that these siRNAs were specific for the human myocilin gene. These candidate siRNAs have neither a sequence similarity to EGFP gene nor the capability of suppressing EGFP expression when tested in cultured cells (data not shown). FIG. 3 depicts the regions of myocilin targeted by siRNAs generated from SiFinder. One siRNA is targeted at the myosin-like domain (R76, siMYOC-A) and the other three are targeted at the olfactomedin region (E352, siMYOC-B; K423, siMYOC-C; and N480, siMYOC-D).

```
siMYOC-A:
5'-aacttacagagagacagcagc-3'      (SEQ ID NO: 1)

siMYOC-B:
5'-aataccgagacagtgaaggct-3'      (SEQ ID NO: 2)

siMYOC-C:
5'-aacatccgtaagcagtcagtc-3'      (SEQ ID NO: 3)

siMYOC-D:
5'-aaccccctggagaagaagctc-3'      (SEQ ID NO: 4)
```

There were other siRNA molecules that met the criteria entered into the SiFinder program, but did not suppress myocilin in vivo. The siRNA molecules that were actually tested, are the following:

```
siMYOC-E:
5'-AAGCAGTCAGTCGCCAATGCC-3'     (SEQ ID NO: 6)

MC-175.5:
5'-GGCCAATGACCAGAGTGGC-3'       (SEQ ID NO: 7)

MC-362.5:
5'-TTGACCTTGGACCAGGCTG-3'       (SEQ ID NO: 8)

MC-553.5:
5'-TCTGGCCAGGAGGTTGGAA-3'       (SEQ ID NO: 9)

MC-800.5:
5'-CTAGTTTGGGTAGGAGAGC-3'       (SEQ ID NO: 10)

MC-1465.5:
5'-CCGCTATAAGTACAGCAGC-3'       (SEQ ID NO: 11)
```

2. Wild-Type Myocilin was Suppressed by siRNA

Figures 4A, 4B:
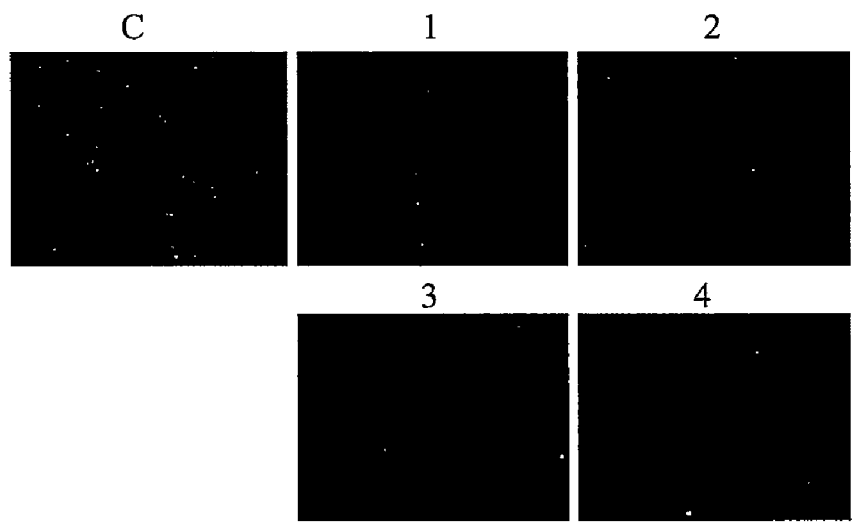
FIG. 4. The suppression of MYOC-EGFP by siRNA specific to the coding region of myocilin in cultured HEK 293 cells. (A) EGFP signals from fluorescence microscopy with same exposure time; control plasmid, C, siMYOCApH1-RNA, 1, siMYOCBpH1-RNA 2, siMYOCCpH1-RNA, 3 and siMYOCDpH1-RNA, 4 (B) western blot of lysates from cultured 293 cells as in (A). 20 μg of proteins from cell lysate was loaded for each lane. The MYOC-EGFP fusion protein bands and β-actin bands were detected with anti-EGFP and anti-β-actin antibodies, respectively.

Co-transfection of siRNA-generating plasmids (siMYO-CpH1-RNA) with MYOCpEGFP was performed in cultured HEK293 cells to evaluate the efficiency of myocilin suppression by myocilin-specific siRNA. GFP fused with myocilin genes enabled us to evaluate the efficiency of siRNA suppression. As shown in As shown in FIG. 4A, siMYOCpH1-A, B, C and D were siRNAs that targeted amino acid residues R76, E352, K423 and N480 of myocilin. FIG. 4A, siMYOC-A, -B, -C and -D co-transfected with MYOCpEGFP showed lower, but variable levels of EGFP fluorescence reduction, when compared with control siRNA. The results indicated successful suppression of myocilin could be achieved by these siRNAs. The expression of wild-type myocilin in cultured HEK 293 cells was significantly suppressed with the siRNAs. FIG. 6 shows the fluorescence signals from MYOC-EGFP were reduced with siMYOCpH1-RNA. Western blot experiments of cell lysates were used to determine the suppression efficiency at protein level. Protein quantification was performed with UN-SCAN-IT software on digitized images.

siMYOCpH1-E failed to suppress the expression of MYOC-EGFP and had similar intensity of MYOC-EGFP compared with control plasmid.

3. Western Blots of HEK 293 Cell Lysates

Western blots of HEK293 cell lysates from co-transfection experiments were also used to determine the suppression efficiency at the protein level. As shown in FIG. 4B, siRNAs targeting regions surrounding residues R76, E352, K423 and N480 were effective in suppressing the expression of the EGFP-myocilin fusion protein. When compared with the control siRNA (FIG. 4B, lane c), the reduction of MYOC-EGFP fluorescence by siMYOC-A, -B, -C and -DpH1-RNA was 79%, 78%, 90%, and 82% respectively (FIG. 4B lanes 1, 2, 3 and 4). The staining intensity of β-actin indicated comparable protein loadings in each sample. The sequences and results of these siRNAs from five independent transfection experiments were summarized in FIG. 5. On average, the inventors achieved about 80 to 90% reduction of myocilin with each of the four siRNA tested. For comparison, the inventors also used a commercial plasmid, pSuper (from Oligoengine, Seattle, Wash.), that generates hairpin siRNAs in vivo via the same mechanism. The results were similar between the pH 1 and pSuper (data not shown).

4. Suppression of Myocilin by siRNA in Cultured TM5 Cells

Figure 6A:
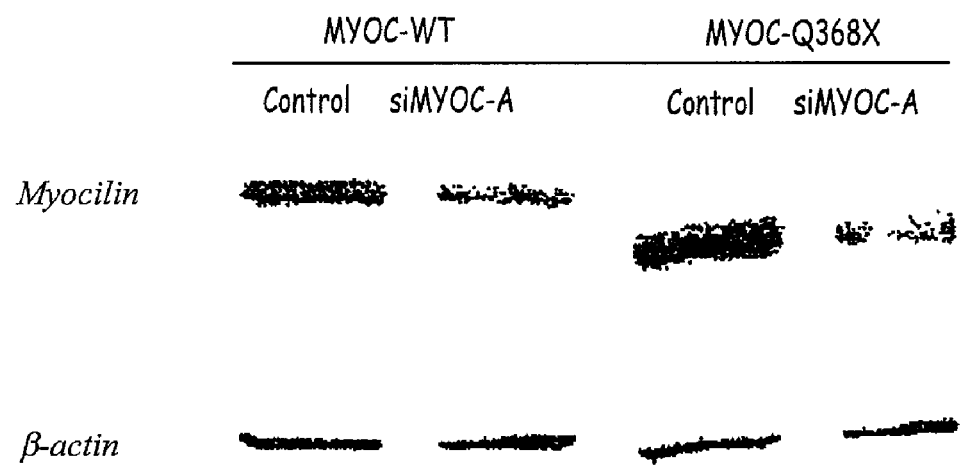
FIG. 6A shows that the MYOC-EGFP fusion protein and β-actin bands were detected with anti-EGFP and anti β-actin antibodies.
Figure 6B:
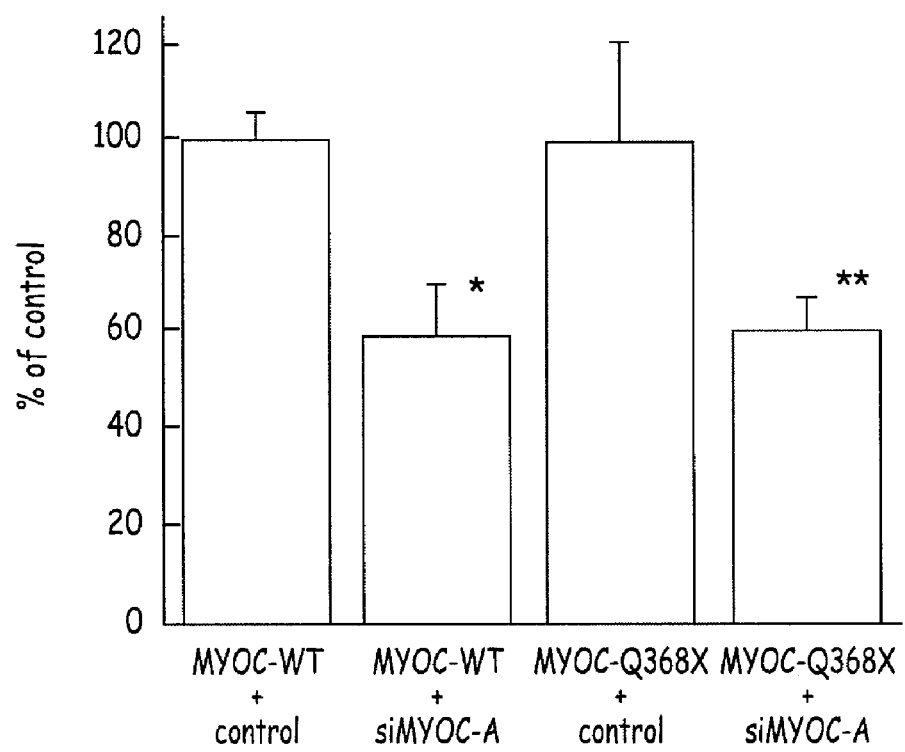
FIG. 6B shows that the expression of myocilin proteins were reduced to 58.9+/−10.6% (*p<0.02) for MYOC-WT and 60.8+/−6.4% (**p<0.03) for MYOC-Q368X, respectively, by siMYOC-A, compared to the control. (n=3, bar=SD).

The inventors also tested the efficacy of these siRNAs in an immortalized TM cell line, TM5. As shown in FIG. 6A, siMYOC-ApH1-RNA effectively suppressed the expression of both MYOC-EGFP (wild type) and the Q368X-EGFP mutant in TM5 cells. The myocilin expression of MYOC-WT and MYOC-Q368X was reduced to 58.9+/−10.6% and 60.8+/−6.4% of control levels, respectively (FIG. 6B) by siMYOC-ApH1-RNA. On average, siMYOC-ApH1-RNA achieved about 40% of myocilin suppression in TM5 cells.

5. Activation of BiP Gene by BiP Promoter-Driven Luciferase Assay

Figure 7:
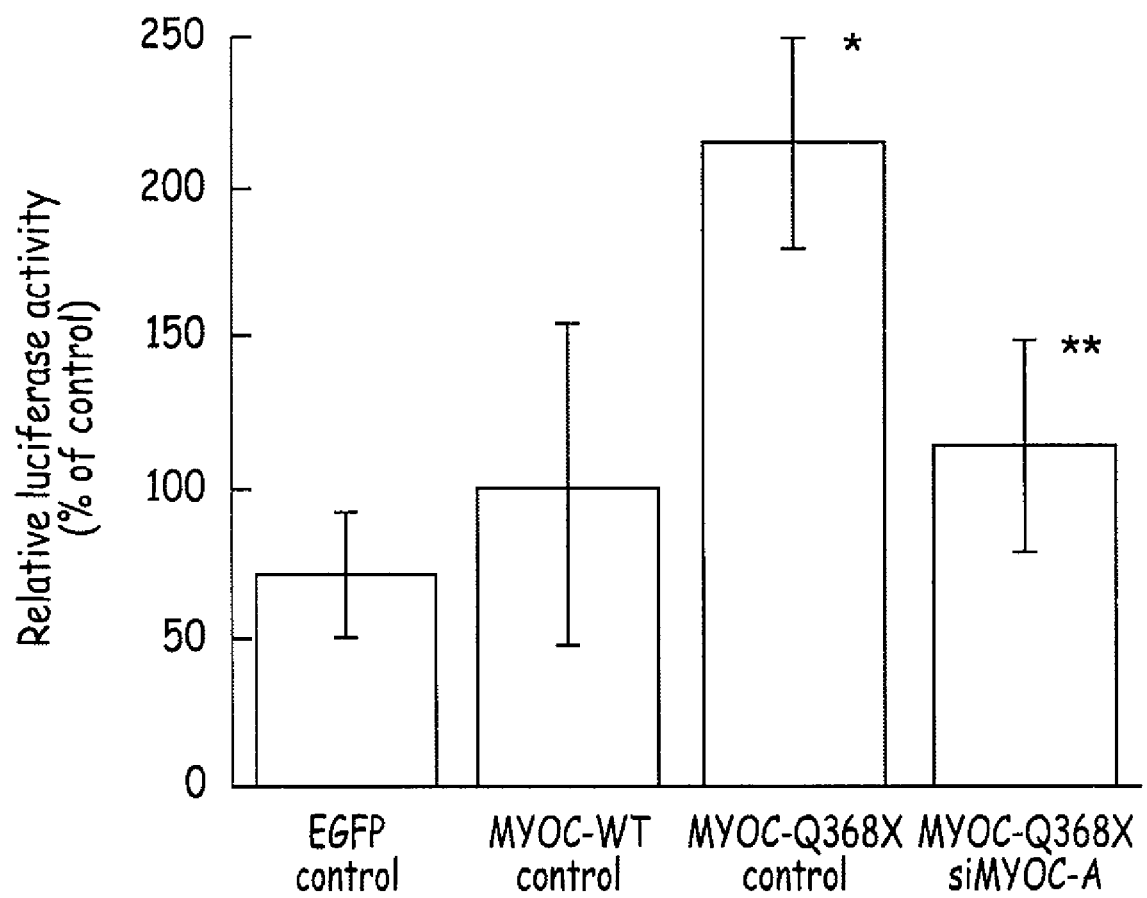
FIG. 7. Luciferase reporter assays of BiP gene activation in TM5 cells. BiPpGl3 vector was co-transfected with either MYOC-WTpEGFP or MYOC-Q368XpEGFP, along with control siRNA or siMYOC-A. 48 hours after transfections, dual luciferase assays were performed on transfected cells. The results were from three independent transfection experiments and each experiment was tested in triplicates. (bar=SD). The reporter activity of MYOC-WT/control was used as the baseline (100%) for comparison. Significant difference between "MYOC-WT/control" and "MYOC-Q368X/control", (*p<0.001) and significant difference between "MYOC-Q368X/control" and "MYOC-Q368X/siMYOC-A" (**p<0.001) were noted. (n=9, bar=SD).

To further study the capability of siRNA in ameliorating the cytotoxic effects induced by mutant myocilins, we investigated the activation of BiP gene, one of the ER stress-response elements, with a BiP promoter-driven luciferase assay. As shown in FIG. 7, transfection of TM5 cells with myocilin wild-type cDNA showed a mild increase of BiP activation when compared with the control pEGFP (containing no myocilin). On the other hand, transfection with mutant Q368X-EGFP resulted in statistically significant activation of BiP when compared to transfection with myocilin wild-type (214% of increase) or EGFP (300% of increase). Most important, co-transfection of Q368X-EGFP and siMYOC-A significantly reduced the activation of BiP by 50% compared to co-transfection with control siRNA. siMYOC-A effectively ameliorated the BiP activation caused by mutant Q368X-EGFP to a level similar to that caused by myocilin wild-type.

C. Discussion

Using a human H1-RNA promoter based vector and the SiFinder web-based program for selecting and designing siRNAs, the inventors have produced several plasmids that generate hairpin RNAs to suppress wild type and mutant myocilins in cultured HEK293 and TM cells. The in vitro experiments of transfecting MYOC-Q368CpEGFP into TM5 cells further reconfirmed the previous notion that mutant myocilins can result in protein misfolding and cause the upregulation of BiP gene (ER stress response) in TM cells. More important, the sequence-specific RNA interference by siRNA can ameliorate the BiP stress response induced by mutant myocilins. In summary, the have identified siRNAs that can be used successfully as effective "molecular silencers" to suppress the expression of myocilin. Potential application of these siRNA to treat myocilin-related glaucoma is currently investigated.

siRNA is a useful tool to silence those untoward gene mutations, especially the ones associated with abnormal protein production, known as gain-of-function. There is strong evidence indicating that myocilin-related glaucoma is probably due to the gain-of-function mechanism rather than loss-of-function:

(A) When cDNAs encoding mutant myocilin were transfected into cultured TM cells, the expressed mutant myocilin proteins failed to be secreted extracellularly and formed aggregates of misfolded proteins inside the TM cells (Jacobson 2001). Evidence indicating the presence of misfolded proteins includes over-expression of αB-crystallin with myocilin in glaucoma patients and co-localization of protein disulfide isomerase (PDI) with aggregated mutant myocilin in ER (Lutjen-Drecoll 1998, Sohn 2002). A recent report further demonstrated that MYOC-Q368X mutant proteins induced the ER stress response as indicated by the activation of grp78 (BiP) in human TM cells (Joe 2003). The present study also confirmed this finding. The mutant myocilins prevented the secretion of wild-type protein when cDNAs of both wild-type and mutant myocilins were co-transfected into cultured TM cells. Since there is direct evidence suggesting that myocilin forms dimers or even oligomers in vivo (Fauss 1993), it is likely that misfolded mutant myocilins bind and trap wild-type proteins inside the cells. It has also been shown that expression of mutant myocilin causes significant cell death in cultured TM cells (Sohn 2002). Loss of TM cells in aged and glaucomatous animals correlates well with increased resistance of aqueous humor outflow and elevated IOP (Russell 2001). Taken together, these data suggest that mutant myocilins are likely to cause cytotoxic effects and cell death in trabecular meshwork.

(B) Myocilin knockouts revealed no discernable phenotype and normal IOP in myocilin-null animals (Kim 2001). Patients with deletion of one myocilin allele also did not develop glaucoma (Wiggs 2001). For patients carrying an Arg46Stop mutation (which results in a severely truncated form of myocilin, missing more than 90% of the amino acid residues of wild-type protein), neither homozygous nor heterozygous patients have any evidence of glaucoma (Lam 2000), except for one case of POAG (Yoon 1999). It was estimated that 3% of the Asian control subjects in one study carry this Arg46Stop mutation without evident glaucoma (Lam 2000). Therefore, the Arg46Stop mutation is considered a polymorphism rather than a glaucoma-causing mutation. Taken together, loss of myocilin does not have a known cytotoxicity or untoward cellular functions. Thereby, myocilin-related glaucoma is not mediated via a loss-of-function mechanism.

To date the inventors have tested 10 myocilin-specific siRNAs, of which four worked well in achieving myocilin suppression. As shown in FIGS. 4 and 5, the suppression efficiencies could be up to a 90% reduction of target myocilins in HEK293 cells. In TM5 cells, the suppression of wild-type and mutant myocilins by siMYOC-A is also effective, although to a lesser extent (~40%, FIG. 6B).

Many myocilin mutations linked to POAG are missense mutations within the olfactomedin domain. Among them, the myocilin Q368X nonsense mutation is one of the most common mutations found in POAG patients. As shown in FIG. 7, suppression of Q368X-EGFP by myocilin-specific siRNA indeed reduced the activation of BiP gene (indicative of reduced ER stress) in TM5 cells.

In summary, we have identified siRNAs that can effectively suppress the expression of myocilin. When combined with high efficiency delivery methods such as virus transduction or nanoparticle technology, this strategy can be potentially an promising gene-modifying therapy for myocilin-related glaucoma.

Example 2

Using Nanoencapsulated Particles to Achieve an Optimal Delivery of siRNA into TM Cells Topical administration of ophthalmic medications to the anterior segment of the eye is an effective method for treating ocular disorders; however, limiting factors such as poor drug permeability or absorption through corneal tissues and rapid tear turnover or nasolacrimal drainage can compromise the optimal effects of topical medications. Furthermore, although promising, topical application of therapeutic genetic materials such as antisense nucleotides, morpholino oligos, siRNAs and plasmids into ocular tissues remains unsatisfactory and requests improved delivery methods with higher specificity and better transfection efficiency.

Compared to commonly used liposome and virus-mediated delivery methods, nanoparticle-mediated drug delivery has become a preferred choice for delivery of drugs or macromolecules due to its low toxicity and high efficiency. For example, successful delivery of the anti-glaucoma agent, Pilocarpine, via the polybutylcyanoacrylate nanoparticles has been reported (Zimmer et al., 1994). The biodegradable nanoparticles made from poly D,L-lactide-co-glycolide (PLGA) have also been shown to transfect rabbit conjunctival epithelial cell layers successfully (Qaddoumi et al., 2004). In contrast to small molecules, macromolecules such as nucleic acids, proteins and peptides present increased challenges for drug delivery because they have limited ability to cross cell membranes, degrade rapidly in the bloodstream, and generally cannot be delivered topically or orally. As a result, many macromolecules must be delivered by injection, often multiple times daily or weekly in large doses to achieve a therapeutic concentration in both research animals and human subjects. Sub-50 nm nanocapsules (nanoCR-s50™) function as effective site-specific drug carriers for macromolecules because they carry the compressed drug cargo (such as DNA, oligonucleotides, or siRNA) into cells via the receptor-mediated caveolar uptake. Nanocapsules can be produced using known methods. See, e.g., PCT/US03/10729, PCT/US03/10854, PCT/US03/10850, and WO00164164. Cellular entry through the tiny caveolae rather than the larger, better-known clathrin-coated pits (endocytosis) has a tremendous benefit, as the clathrin-coated pits and endosomes morph into acidic lysosomes over time, eventually destroying their contents for recycling. The key to effective biologic drug delivery as in the caveolin-mediated pathway is to avoid lysosomes and related intracellular degradation (Bally et al., 1998).

Caveolae traffic their contents throughout the cell. Because of the lipid nature of caveolae, receptors known to populate or traffic to caveolae following ligand binding include those with fatty acid tails such as GPI-linked or integrin receptors. An integral role for caveolin in mediating β1 integrin signaling and maintaining focal adhesions has been documented (Wei et al., 1999). Every cell type examined to date, including lymphocytes, has been found to contain either caveolae or caveolae-like structures (Harris et al., 2002). In some tissues such as liver, other members of the caveolin family can substitute for caveolin-1 in stabilizing the caveolae walls (Volonte et al., 1999). The receptor-mediated nature of caveolar uptake means that one can direct nanocapsules to selected cells or tissues via judicious capsule designs using ligand-mediated targeting. Once a target receptor is identified, capsules are made from natural or receptor-specific ligands, such as peptides. Manufacturing sub-50 nanocapsules involves building a capsule around the drug molecule and crystallizing it to induce stability. Molecules as large as 500 kD and plasmid DNA as large as 10 KB have been compressed into 25 nm capsules. Capsule stability is excellent at lowered temperatures and capsules can be lyophilized and reconstituted (Derwent, 2001; Unger 2001). Tracking studies show that sub-50 nanocapsules are transported to the cell nucleus, where they dissolve to release their compressed drug cargo, creating an ideal vehicle for nucleus-targeting drugs (Unger, 2001). Those drug species that do not bind in the nucleus are subsequently transported to the cytoplasm, enabling an indirect route to the cytoplasm.

A very important feature of sub-50 nanocapsules is that they exhibit the efficient transport properties of those associated with low molecular weight compounds (i.e., small molecules). In vitro studies showed 100% uptake efficiencies in cell culture (Unger, 2001). Complete penetration through pig epidermis and intra-arterial penetration to outer edges of large arteries were noted in organ cultures.

RGD peptide-encapsulated nanoCR-s50 particles have been produced and achieved high transfection efficiency with minimal cytotoxicity in the TM5 cell line. siRNAs encapsulated in tissue-specific nanoCR-s50 particles are used to suppress high expression in cultured limbal explant or myocilin expression in cultured TM, using ex vivo organ cultures or anterior chamber perfusion.

Manufacture of Nanoparticle

The siRNA-generating plasmid or luciferase reporter gene are encapsulated with either RGD peptide or the identified peptide ligands for limbal and TM cells (capsule), according to the protocol set forth in Unger, U.S. Pat. No. 6,632,671 B2. The size of nanocapsule from each batch is determined by a Dimension 3100 Atomic Force Microscope. The size distribution and surface zeta potential profile is investigated with a Zetasizer Nano ZS (Malvern Instrument Inc., Southborough, Mass.). Nanocapsules are lyophilized and stored at −20° C. until use.

a. Manufacturing NanoCr-s50 with RGD Peptides as Encapsulation Materials.

The inventors manufactured nanoCR™ s50-nanocapsules (Unger, 2001). In brief, s50-nanocapsules were produced by "dispersion atomization" by 1) dispersing nucleic acid complexed with cationic polymer into water using a water-insoluble surfactant system (<500 ppm), 2) emulsifying dispersed nucleic acid with a water-miscible solvent (<0.2% total phase volume), 3) inverting emulsion with water addition, 4) coating hydrophobic micelles by hydrophillic polymer addition and adsorption, 5) atomizing protein-coated micelles into a salt receiving solution. Following incubation, particles were collected by centrifugation for final processing. Particle size was calculated as the average elliptical axis from image analysis of atomic force microscopy data collected in tapping mode. In general, this process achieved an additional 50% condensation in particle size compared to simple polymeric complexes and small liposomes that we believe relates to interaction of cations with nucleic acids constrained to a surface (Manning condensation) (Koltover et al., 2000).

The inventors also manufactured nanocapsules containing nanocrystal fluorophores, Quantum-dot (Evident Technologies) or 4.5 kB luciferase reporter plasmid using either the fully hydrophilic peptide RGDS or the hydrophobic cyclic peptide RGD-PV (Peptide-2000™). RGD peptides can mediate the uptake of nanoencapsulated particles via binding integrin receptors on cell membrane. It has been a versatile tool for nanoencapsulation due to its broad specificity toward most cells tested so far. Micrographs of Atomic Force Microscopy (s50 nanocapsules bearing nucleic acids made from peptide containing hydrophilic and hydrophobic domains) indicated that the hydrophilic peptide produced a slightly larger capsule, but that both peptides produce nanocapsules well under an average dry diameter of 50 nm (RGDs vs. cyclic RGD-PV: 13±2 vs. 10±2 nm) as calculated by image analysis. Peptides containing hydrophobic domains have been problematic to formulate due to issues deriving from aggregation of hydrophobic domains in aqueous systems (Lackey, 2002). From the inventors' results, the hydrophobic RGD-PV can be manufactured into sub-50 nm nanoparticles as well. To date, particles show excellent freeze-thaw stability, stability at −4° C., mechanical stability and tolerate speed-vac lyophilization. Stability was measured by retention of particle size distribution and biological activity. Drug stocks of 3 mg/ml are routinely produced with 70 to 100% yields.

b. Presence of Caveolae/Caveolin-1 in TM Cells.

Although every type of cells examined by Harris et al. has been found to contain either caveolae or caveolae-like structures (Harris et al., 2002), the extent of caveolae contained by each cell type varied greatly. The extent of caveolaes in cells was pivotal for the efficiency of nanocapsule-mediated delivery. The inventors observed that epithelial cells such as dermal, limbal and conjunctival keratinocytes contain abundant caveolae whereas endothelial cells have significantly less amount of caveolae. Fibroblasts and cardiac myocytes, on the other hand, had only minimal stainings when probed with anti-caveolin antibody. Micrographs showed the immunohistochemical studies on limbal epithelial cells from explant culture and TM5 cells with anti-caveolin-1 antibody. Strong punctate signals within limbal cells were observed. The basal layer of limbal epithelia also displayed positive stainings by anti-caveolin-1 antibody. Moderate staining of TM5 cells was also noted. A cross-section of human cornea stained with the anti-caveolin-1 antibody showed that caveolin is present in predominantly in basal limbal epithelial cells and not in stromal fibroblasts.

c. Transfection of TM5 Cell by NanoCR-s5 Particles.

To evaluate the potential of nanoCR-s50 as a delivery vehicle to target TM cells, we added RGD peptide-encapsulated nanoCR-s50 containing Quantum-dot nanocrystals to the cultured TM5 cells. After 48 hours, cells were observed for the fluorescence signals from Quantum-dot without fixing (the water soluble Quantum-dot nanocrystals diffuse out of cell during fixation process). A high percentage of cells (>90%) displayed nuclear or cytosolic accumulation of fluorophores indicating the success of nanocapsulated particles in delivery cargo content into TM5 cells. TM5 cells treated with nanoCR-s50 containing Quantum-dot were observed for fluorescence signals (FITC) or Hoechst (DAPI for nucleus). There was no significant cell death in cells treated with nanocapsulated particles after 48 hours. TM5 cell transfected with liposomes or lentivirus, on the other hands, usually had more cell death when treated with various dosages (unpublished observations).

Example 3

Delivery of Nanocapsules to Explant and Organ Culture

Cultured cells as well as organ culture are used as model systems to test the nanocapsules.

(1) NanoCR-s50 for delivering siRNA into cultured TM and limbal cells. After adding the nanoCR-s50 particles into cultured TM and limbal cells, fluorescent microscopy and Western blotting is performed at various set times to evaluate the suppression efficiency. The time for cargo DNA to be transported into nuclei ranges from 16 hours to days. According to the inventors' previous experience, it is not necessary to remove the nanoCR-s50 from the medium due to its low toxicity.

(2) Direct application or perfusion of nanoCR-s50. The nanoCR-s50 containing luciferase reporter gene (as the reporter) is either applied directly to the topical epithelia or injected into the anterior chamber by perfusion. In skin, absorption of nanoCR-s50 into dermal tissues can be achieved simply by applying solution drops onto the target area. A microperfusion pump will be connected to perfuse the eye with medium at 2.5 ml/min, which is the normal outflow rate for human anterior chamber. For the dose-response experiments, various concentrations of nanoCR-s50 are mixed with the medium and delivered in the afferent perfusate. The histological evaluation of the limbus and perfused TM will be performed 3 to 7 days after application of nanoCR-s50 by immunohistochemical staining with anti-luciferase, anti-myocilin and anti-bigh3 antibodies.

REFERENCES

Bally et al., *Adv. Drug Del. Rev.* 30: 291-315 (1998).
Brummelkamp et al., *Science,* 296, 550-553 (2002).
Caballero and Borras, *Biochem. Biophys. Res. Comm.,* 282, 662-670 (2001).
Derwent, D., 2001. Recent patents in drug delivery. Nature Biotech 20: 93.
Elbashire et al., *Nature,* 411, 494-498 (2001).
Fauss et al. Lutjen-Drecoll, E. (Ed.), Basic Aspects of Glaucoma Research III., Schattauer Verlag, New York, N.Y., pp 319-330 (1993).
Fingert et al. Myocilin Glaucoma. *Surv Ophthalmol* 47: 547-561 (2002).
Fautsch and Johnson, *Invest. Ophthalmol. Vis. Sci.,* 42(10), 2324-2331 (2001).
Fire et al., *Nature,* 391, 806-811 (1998).
Hamilton and Baulcombe, *Science,* 286, 950-952 (1999).
Harris et al., *Immunol.* 105: 190-195 (2002).
Hohjoh H., *FEBS Lett.* 521, 195-9 (2002).
Jacobson et al., *Hum. Mol. Genet.,* 10, 117-125 (2001).
Joe et al., *Biochem Biophys Res Commun* 312: 592-600 (2003).
Kahn and Milton, *Am. J. Epidemiol.,* 111, 769-776 (1980).
Kim et al., *Mol. Cell. Biol.,* 21(22), 7707-7713 (2001).
Koltover et al., *Proc Natl Acad Sci USA.* 97(26):14046-51 (2000)
Lam et al., *Invest Ophthalmol Vis Sci* 41: 1386-1391 (2000).
Lipardi et al. *Cell* 107: 297-307 (2001).
Lutjen-Drecoll et al., *Invest Ophthalmol Vis Sci* 39: 517-525 (1998).
Martinez et al., *Proc Natl Acad Sci* 99: 14849-14854 (2002).
Miller et al., *Proc Natl Acad Sci* 100: 7195-7200 (2003).
Morcos, *Genesis,* 30, 94-102 (2001).
Ortego et al., *FEBS Letters,* 413, 349-353 (1997).
Paddison et al., *Genes & Dev.,* 16, 948-958 (2002).
Pang et al., *Curr Eye Res* 13: 51-63 (1994).
Polansky et al., *Invest Ophthalmol Vis Sci.,* 18, 1043-1049 (1979).
Polansky et al., *Ophthalmology,* 91, 558-595 (1984).
Qaddoumi et al., *Pharm Res.* 21(4):641-8 (2004).
Russel et al., *Invest. Ophthalmol. Vis. Sci.,* 42, 983-986 (2001).
Sohn et al., *Invest. Ophthalmol. Vis. Sci.,* 43(12), 3680-3685 (2002).
Stone et al., *Science,* 275(5300), 668-670 (1997).
Szczesna-Skorupa et al., *J Biol Chem* 279: 13953-13961 (2004).
Tamm et al., *Prog. in Retinal and Eye Res.,* 21, 395-428 (2002).
Ueda et al., *Invest Ophthalmol Vis Sci* 44: 4772-4779 (2003).
Unger et al., *AAPS Pharmsci* 3: 3731 (2001).
Volonte et al., *J. Biol. Chem.* 274: 12702-12709 (1999).
Wei et al., *J. Cell. Biol.,* 144: 1285-1294 (1999).
Wiggs and Vollrath, *Arch. Ophthalmol.,* 119, 1674-1678 (2001).
Wordinger et al., *Invest Ophthalmol Vis Sci* 41: 3833-3841 (2000).
Yoon et al., *Korea. Am J Hum Genet* 64: 1775-1778 (1999).
Yu et al., *Proc. Natl. Acad. Sci.,* 99, 6047-6052 (2002).
Zimmer et al., *Pharm. Res.* 11(9): 1435-1442 (1994).

The invention is described with reference to various specific and preferred embodiments and techniques. However, it should be understood that many variations and modifications may be made while remaining within its scope. All referenced publications, patents and patent documents are intended to be incorporated by reference, as though individually incorporated by reference.

---

SEQUENCE LISTING

<160> NUMBER OF SEQ ID NOS: 19

<210> SEQ ID NO 1
<211> LENGTH: 21
<212> TYPE: DNA
<213> ORGANISM: Artificial
<220> FEATURE:
<223> OTHER INFORMATION: Oligonucleotide

<400> SEQUENCE: 1
aacttacaga gagacagcag c                                              21

```
<210> SEQ ID NO 2
<211> LENGTH: 21
<212> TYPE: DNA
<213> ORGANISM: Artificial
<220> FEATURE:
<223> OTHER INFORMATION: Oligonucleotide

<400> SEQUENCE: 2
aataccgaga cagtgaaggc t                                              21

<210> SEQ ID NO 3
<211> LENGTH: 21
<212> TYPE: DNA
<213> ORGANISM: Artificial
<220> FEATURE:
<223> OTHER INFORMATION: Oligonucleotide

<400> SEQUENCE: 3
aacatccgta agcagtcagt c                                              21

<210> SEQ ID NO 4
<211> LENGTH: 21
<212> TYPE: DNA
<213> ORGANISM: Artificial
<220> FEATURE:
<223> OTHER INFORMATION: Oligonucleotide

<400> SEQUENCE: 4
aaccccctgg agaagaagct c                                              21

<210> SEQ ID NO 5
<211> LENGTH: 21
<212> TYPE: DNA
<213> ORGANISM: Artificial
<220> FEATURE:
<223> OTHER INFORMATION: Oligonucleotide

<400> SEQUENCE: 5
aacagtcgcg tttgcgactg g                                              21

<210> SEQ ID NO 6
<211> LENGTH: 21
<212> TYPE: DNA
<213> ORGANISM: Artificial
<220> FEATURE:
<223> OTHER INFORMATION: Oligonucleotide

<400> SEQUENCE: 6
aagcagtcag tcgccaatgc c                                              21

<210> SEQ ID NO 7
<211> LENGTH: 19
<212> TYPE: DNA
<213> ORGANISM: Artificial
<220> FEATURE:
<223> OTHER INFORMATION: Oligonucleotide

<400> SEQUENCE: 7
ggccaatgac cagagtggc                                                 19

<210> SEQ ID NO 8
<211> LENGTH: 19
<212> TYPE: DNA
<213> ORGANISM: Artificial
<220> FEATURE:
```

-continued

```
<223> OTHER INFORMATION: Oligonucleotide

<400> SEQUENCE: 8
ttgaccttgg accaggctg                                                      19

<210> SEQ ID NO 9
<211> LENGTH: 19
<212> TYPE: DNA
<213> ORGANISM: Artificial
<220> FEATURE:
<223> OTHER INFORMATION: Oligonucleotide

<400> SEQUENCE: 9
tctggccagg aggttggaa                                                      19

<210> SEQ ID NO 10
<211> LENGTH: 19
<212> TYPE: DNA
<213> ORGANISM: Artificial
<220> FEATURE:
<223> OTHER INFORMATION: Oligonucleotide

<400> SEQUENCE: 10
ctagtttggg taggagagc                                                      19

<210> SEQ ID NO 11
<211> LENGTH: 19
<212> TYPE: DNA
<213> ORGANISM: Artificial
<220> FEATURE:
<223> OTHER INFORMATION: Oligonucleotide

<400> SEQUENCE: 11
ccgctataag tacagcagc                                                      19

<210> SEQ ID NO 12
<211> LENGTH: 105
<212> TYPE: DNA
<213> ORGANISM: Artificial
<220> FEATURE:
<223> OTHER INFORMATION: Oligonucleotide

<400> SEQUENCE: 12
taatatttgc atgtcgctat gtgttctggg aaatcaccat aaacgtgaaa tgtctttgga        60
tttgggaatc ttataagttc tgtatgagac cactctttcc cgggc                       105

<210> SEQ ID NO 13
<211> LENGTH: 107
<212> TYPE: DNA
<213> ORGANISM: Artificial
<220> FEATURE:
<223> OTHER INFORMATION: Oligonucleotide

<400> SEQUENCE: 13
tcgagcccgg gaaagagtgg tctcatacag aacttataag attcccaaat ccaaagacat        60
ttcacgttta tggtgatttc ccagaacaca tagcgacatg caaatat                     107

<210> SEQ ID NO 14
<211> LENGTH: 9
<212> TYPE: DNA
<213> ORGANISM: Artificial
<220> FEATURE:
<223> OTHER INFORMATION: Oligonucleotide

<400> SEQUENCE: 14
```

```
<210> SEQ ID NO 15
<211> LENGTH: 9
<212> TYPE: DNA
<213> ORGANISM: Artificial
<220> FEATURE:
<223> OTHER INFORMATION: Oligonucleotide

<400> SEQUENCE: 15 ttcagaagg                                                                  9

<210> SEQ ID NO 16
<211> LENGTH: 6
<212> TYPE: DNA
<213> ORGANISM: Artificial
<220> FEATURE:
<223> OTHER INFORMATION: Oligonucleotide

<400> SEQUENCE: 16 attttt                                                                     6

<210> SEQ ID NO 17
<211> LENGTH: 21
<212> TYPE: DNA
<213> ORGANISM: Artificial
<220> FEATURE:
<223> OTHER INFORMATION: Oligonucleotide

<400> SEQUENCE: 17
aacagtcgcg tttgcgactg g                                                   21

<210> SEQ ID NO 18
<211> LENGTH: 28
<212> TYPE: DNA
<213> ORGANISM: Artificial
<220> FEATURE:
<223> OTHER INFORMATION: Oligonucleotide

<400> SEQUENCE: 18
ggctggatcc atcttggaga gcttgatg                                            28

<210> SEQ ID NO 19
<211> LENGTH: 28
<212> TYPE: DNA
<213> ORGANISM: Artificial
<220> FEATURE:
<223> OTHER INFORMATION: Oligonucleotide

<400> SEQUENCE: 19
gaagaattca tgaggttctt ctgtgcac                                            28
``` ttcaagaga                                                                  9

What is claimed is:

1. An isolated myocilin-specific ribonucleic acid (RNA), wherein the RNA is a double-stranded molecule with a first strand of RNA that is a ribonucleotide sequence that corresponds to a nucleotide sequence encoding myocilin and a second strand of RNA that is a ribonucleotide sequence that is complementary to the nucleotide sequence encoding myocilin, wherein the first and the second ribonucleotide strands are complementary strands that hybridize to each other to form the double-stranded molecule, wherein the RNA comprises less than 30 bp and has 21 contiguous nucleotides encoded by SEQ ID NOs. 1, 2, 3 or 4 and wherein the double-stranded molecule suppresses accumulation of myocilin in a trabecular meshwork (TM) cell.

2. The myocilin-specific RNA of claim 1, wherein the RNA is encapsulated in a nanoparticle.

3. A purified myocilin-specific double stranded RNA wherein, the RNA comprises less than 30 bp and has 21 contiguous nucleotides of SEQ ID NOs. 1, 2, 3 or 4.

4. The myocilin-specific RNA of claim 3, wherein the RNA is encapsulated in a nanoparticle.

5. An isolated myocilin specific double stranded RNA expressed in a cell comprising:

(a) a vector including a target sequence comprising a coding region of a myocilin gene, wherein the target sequence comprises RNA comprising less than 30 bp and has 21 contiguous nucleotides of SEQ ID NOs. 1, 2, 3 or 4;

(b) the target sequence further comprising a linker sequence between a sense and an antisense strand of the coding region;

(c) wherein the target sequence is inserted in the vector under the control of an RNA promoter and transfected into a cell or organism;

(d) wherein transcription of the target sequence provides the double stranded RNA.

6. The isolated myocilin-specific double stranded RNA of claim 5, wherein in step (d) transcription results in a short hairpin RNA that is processed by an enzyme to result in a double stranded siRNA.

7. The isolated myocilin specific double stranded RNA of claim 5, wherein the target sequence is SEQ ID NO: 1, SEQ ID NO: 2, SEQ ID NO: 3, SEQ ID NO: 4 or combinations thereof.

8. A method of suppressing the accumulation of myocilin in an ocular tissue cell comprising introducing a ribonucleic acid (RNA) into the cell in an amount sufficient to suppress accumulation of myocilin, wherein the RNA is a double-stranded molecule with a first strand of RNA that is a ribonucleotide sequence that corresponds to a nucleotide sequence encoding myocilin and a second strand of RNA that is a ribonucleotide sequence that is complementary to the nucleotide sequence encoding myocilin, wherein the RNA comprises less than 30 bp and has 21 contiguous nucleotides encoded by SEQ ID NOs. 1, 2, 3 or 4, wherein the first and the second ribonucleotide strands are complementary strands that hybridize to each other to form the double-stranded molecule, and wherein the double-stranded molecule suppresses accumulation of myocilin in the ocular tissue cell.

9. The method of claim 8 in which accumulation of myocilin is suppressed by at least 10%.

10. A method to inhibit expression of a myocilin gene in an ocular tissue cell comprising introducing a ribonucleic acid (RNA) into the cell in an amount sufficient to inhibit expression of the myocilin gene, wherein the RNA is a double-stranded molecule with a first strand that is a ribonucleotide sequence that corresponds to a nucleotide sequence of the myocilin gene and a second strand that is a ribonucleotide sequence that is complementary to the nucleotide sequence of the myocilin gene, wherein the RNA comprises less than 30 bp and has 21 contiguous nucleotides encoded by SEQ ID NOs. 1, 2, 3 or 4, wherein the first and the second ribonucleotide strands hybridize to each other to form the double-stranded molecule, and wherein the double-stranded molecule inhibits expression of the myocilin gene.

11. The method of 10, wherein the ocular tissue cell is in a mammal.

12. A method to inhibit expression of a myocilin gene in a mammal comprising:

(a) providing a mammal containing an ocular tissue cell, wherein the cell contains the myocilin gene and the ocular tissue cell is susceptible to RNA interference, and the myocilin gene is expressed in the ocular tissue cell;

(b) contacting the mammal with a ribonucleic acid (RNA), wherein the RNA is a double-stranded molecule with a first strand that is a ribonucleotide sequence that corresponds to a nucleotide sequence of the myocilin gene and a second strand that is a ribonucleotide sequence that is complementary to the nucleotide sequence of the myocilin gene, wherein the RNA comprises less than 30 bp and has 21 contiguous nucleotides encoded by SEQ ID NOs. 1, 2, 3 or 4, and wherein the first and the second ribonucleotide sequences are complementary strands that hybridize to each other to form the double-stranded molecule, thereby inhibiting expression of the myocilin gene, wherein the contacting is achieved by topical administration to the eye of the mammal.

13. The method of claim 12, in which expression of myocilin is inhibited by at least 10%.

14. The method of claim 12, wherein the mammal is a human.

15. The method of claim 12, wherein the ocular tissue cell is conjunctiva, sclera, trabecular meshwork (TM) or cornea.

16. The method of claim 12, wherein the ocular tissue cell is TM.

17. The method of claim 12, wherein the topical administration comprises drops or injections around the eye.

18. The method of claim 12, wherein the myocilin is a mutant myocilin.

19. A method of treating glaucoma in a patient in need thereof comprising topically administering to the eye of the patient a ribonucleic acid (RNA) in an amount sufficient to suppress accumulation of myocilin in an ocular tissue cell, wherein the RNA is a double-stranded molecule with a first strand of RNA that is a ribonucleotide sequence that corresponds to a nucleotide sequence encoding myocilin and a second strand of RNA that is a ribonucleotide sequence that is complementary to the nucleotide sequence encoding myocilin, wherein the first and the second ribonucleotide strands are complementary strands that hybridize to each other to form the double-stranded molecule, and wherein the double-stranded molecule suppresses accumulation of myocilin in the ocular tissue cell, wherein the RNA comprises less than 30 bp and has 21 contiguous nucleotides encoded by SEQ ID NOs. 1, 2, 3 or 4.

20. The method of claim 19, wherein the ocular tissue cell is conjunctiva, sclera, trabecular meshwork (TM) or cornea.

21. The method of claim 19, wherein the myocilin is a mutant myocilin.

22. The method of claim 19, wherein the RNA is encapsulated in a nanoparticle.

23. The method of claim 19, wherein the topical administration comprises drops or injections around the eye.

* * * * *

UNITED STATES PATENT AND TRADEMARK OFFICE
CERTIFICATE OF CORRECTION

PATENT NO. : 7,700,575 B2  Page 1 of 1
APPLICATION NO. : 11/546940
DATED : April 20, 2010
INVENTOR(S) : Andrew Huang et al.

It is certified that error appears in the above-identified patent and that said Letters Patent is hereby corrected as shown below:

Title page, Item (12) and Item (76), "Huang Andrew" delete and insert -- Andrew Huang --

Signed and Sealed this

Twentieth Day of July, 2010

David J. Kappos
*Director of the United States Patent and Trademark Office*